(12) United States Patent
Neumann

(10) Patent No.: US 12,346,831 B2
(45) Date of Patent: Jul. 1, 2025

(54) METHODS AND SYSTEMS FOR PHYSIOLOGICALLY INFORMED GESTATIONAL INQUIRIES

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 18/387,314

(22) Filed: Nov. 6, 2023

(65) Prior Publication Data

US 2024/0078451 A1    Mar. 7, 2024

Related U.S. Application Data

(63) Continuation-in-part of application No. 17/884,754, filed on Aug. 10, 2022, now Pat. No. 11,829,895, and
(Continued)

(51) Int. Cl.
*G06N 5/04* (2023.01)
*G06N 20/00* (2019.01)
(Continued)

(52) U.S. Cl.
CPC ............... *G06N 5/04* (2013.01); *G06N 20/00* (2019.01); *G16H 30/20* (2018.01); *G16H 50/20* (2018.01)

(58) Field of Classification Search
CPC .......... G06N 5/04; G06N 20/00; G16H 30/20; G16H 50/20
See application file for complete search history.

(56) References Cited

U.S. PATENT DOCUMENTS 10,068,277 B2    9/2018  Jurgenson et al.
10,553,320 B1 *  2/2020  McNair ................. G16H 10/60
(Continued)

FOREIGN PATENT DOCUMENTS

AU    2015246142    5/2016

OTHER PUBLICATIONS

Robinson, What can I eat in pregnancy? App aims to answer with help from IBM's Watson, Website Article, Dec. 2015 https://www.theguardian.com/sustainable-business/2015/dec/21/what-eat-pregnancy-app-nutrino-ibm-watson-supercomputer.
(Continued)

*Primary Examiner* — Thai Q Tran
*Assistant Examiner* — Jose M Mesa
(74) *Attorney, Agent, or Firm* — Caldwell Intellectual Property Law

(57) ABSTRACT

An apparatus for physiologically informed gestational inquiries is disclosed. The apparatus includes at least a processor and memory communicatively connected to the at least a processor. The memory instructs the processor to receive a biological extraction from the user. The memory instructs the processor to receive a gestational inquiry from the user. The memory instructs the processor to separate the gestational inquiry from a description of the gestational inquiry. The memory instructs the processor to determine a gestational target as a function of the gestational inquiry and the biological extraction. The memory instructs the processor to generate a gestational report as a function of the gestational target.

20 Claims, 12 Drawing Sheets

Related U.S. Application Data a continuation of application No. 16/778,847, filed on Jan. 31, 2020, now Pat. No. 11,468,347.

(51) Int. Cl.
*G16H 30/20* (2018.01)
*G16H 50/20* (2018.01)

(56) References Cited

U.S. PATENT DOCUMENTS

| | | |
|---|---|---|
| 2011/0145017 A1 | 6/2011 | Lee |
| 2012/0173336 A1 | 7/2012 | Strumolo |
| 2014/0156295 A1 | 6/2014 | Cooper |
| 2015/0262249 A1 | 9/2015 | Wical |
| 2015/0364057 A1 | 12/2015 | Catani et al. |
| 2021/0118574 A1* | 4/2021 | Peri .......................... G06N 5/04 |
| 2023/0140653 A1* | 5/2023 | Moufarrej ............... A61P 15/00 435/6.11 |

OTHER PUBLICATIONS

Garcia et al., Must-Have Apps for a Healthy Pregnancy, Website Article, 2019 https://www.parents.com/fun/entertainment/gadgets/must-have-healthy-pregnancy-apps/.

* cited by examiner

METHODS AND SYSTEMS FOR PHYSIOLOGICALLY INFORMED GESTATIONAL INQUIRIES

CROSS-REFERENCE TO RELATED APPLICATIONS

This application is a continuation in part of Non-provisional application Ser. No. 17/884,754 filed on Aug. 10, 2022, and entitled "METHODS AND SYSTEMS FOR PHYSIOLOGICALLY INFORMED GESTATIONAL INQUIRIES," which is a continuation of Non-provisional application Ser. No. 16/778,847 filed on Jan. 31, 2020, and entitled "METHODS AND SYSTEMS FOR PHYSIOLOGICALLY INFORMED GESTATIONAL INQUIRIES," both of which are incorporated herein by reference in their entirety.

FIELD OF THE INVENTION

The present invention generally relates to the field of artificial intelligence. In particular, the present invention is directed to methods and systems for physiologically informed gestational inquiries.

BACKGROUND

Incorrect utilization of products and participation in activities during gestation can have lasting effects. Frequently, decisions made during gestation are uninformed or based off of inconsistent prior findings. There remains to be seen, an ability to determine if products and services are compatible for a user and also compatible based on the gestational phase of the user.

SUMMARY OF THE DISCLOSURE

An apparatus for physiologically informed gestational inquiries is disclosed. The apparatus includes at least a processor and memory communicatively connected to the at least a processor. The memory instructs the processor to receive a biological extraction from the user. The memory instructs the processor to receive a gestational inquiry from the user. The memory instructs the processor to separate the gestational inquiry from a description of the gestational inquiry. The memory instructs the processor to determine a gestational target as a function of the gestational inquiry and the biological extraction. The memory instructs the processor to generate a gestational report as a function of the gestational target.

An method for physiologically informed gestational inquiries is disclosed. The method includes receiving, using at least a processor, a biological extraction from the user. The method includes receiving, using the at least a processor, a gestational inquiry from the user. The method includes separating, using the at least a processor, the gestational inquiry from a description of the gestational inquiry. The method includes determining, using the at least a processor, a gestational target as a function of the gestational inquiry and the biological extraction. The method includes generating, using the at least a processor, a gestational report as a function of the gestational target.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for physiologically informed gestational inquiries. In an embodiment, a computing device generates a classification algorithm to calculate a gestational phase. A computing device receives a gestational inquiry containing a question or inquiry related to any aspect of a user's life. For instance and without limitation, a gestational inquiry may seek to uncover what types of cosmetics are safe to be used during pregnancy including any time during preconception and anytime during the postpartum when a user may be breastfeeding. In yet another non-limiting example, a gestational inquiry may contain a question seeking to determine what types of physical activity a user can perform who is currently pregnant and in the first trimester. Computing device classifies a gestational inquiry to an inquiry category. Computing device selects a gestational machine-learning model that utilizes a user biological extraction as an input and outputs one or more indicators of gestational eligibility. Computing device determines utilizing a gestational machine-learning model the gestational eligibility of a gestational inquiry.

Additionally, an apparatus for physiologically informed gestational inquiries is disclosed. The apparatus includes at least a processor and memory communicatively connected to the at least a processor. The memory instructs the processor to receive a biological extraction from the user. The memory instructs the processor to receive a gestational inquiry from the user. The memory instructs the processor to separate the gestational inquiry from a description of the gestational inquiry. The memory instructs the processor to determine a gestational target 168 as a function of the gestational inquiry and the biological extraction. The memory instructs the processor to generate a gestational report as a function of the gestational target 168.

Figure 1:
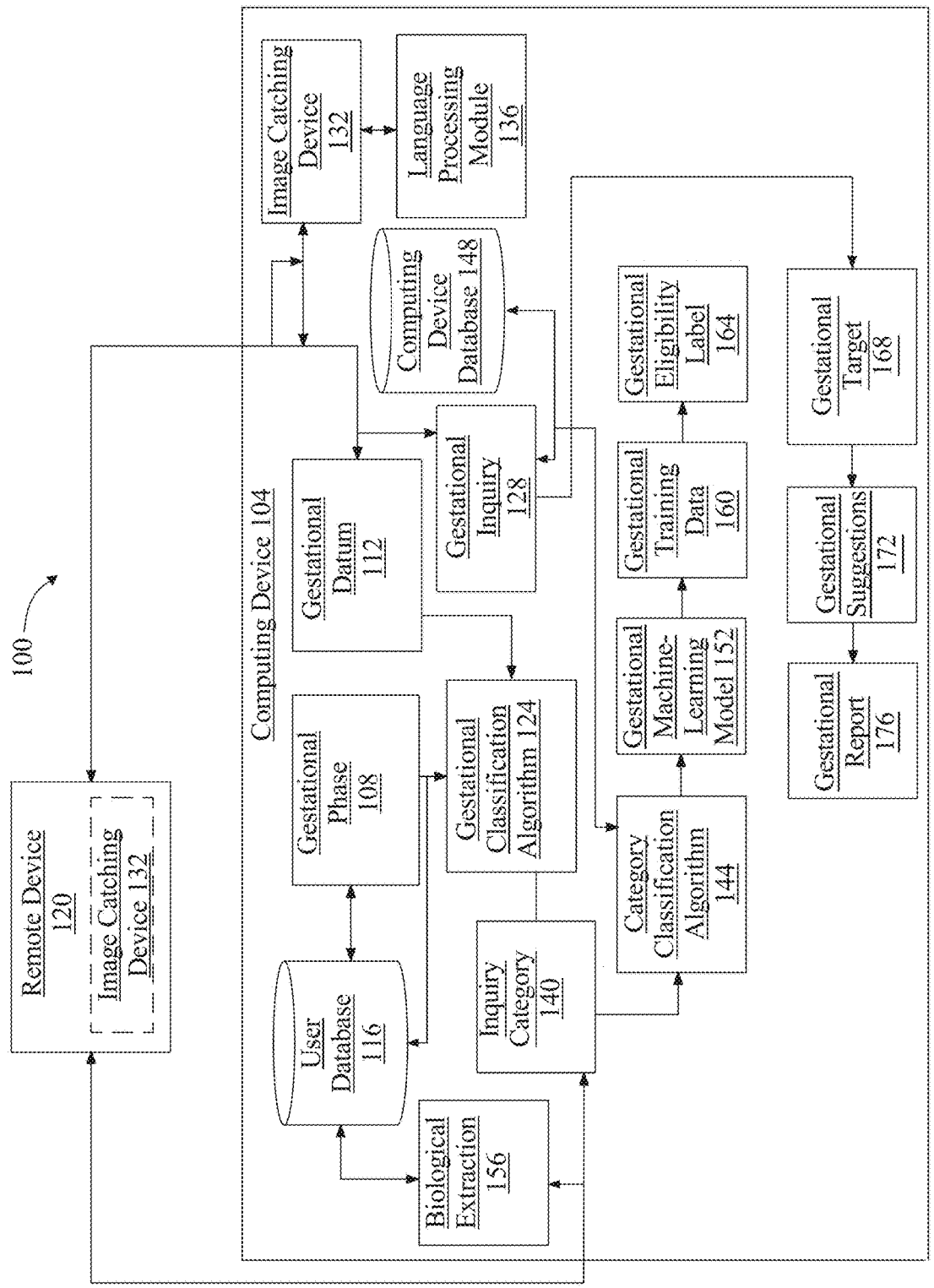
FIG. 1 is a block diagram illustrating an exemplary embodiment of a system for physiologically informed gestational inquiries.

Referring now to FIG. 1, an exemplary embodiment of a system 100 for physiologically informed gestational inquiries is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to calculate a gestational phase 108. A "gestational phase," as used in this disclosure, is any data describing a pregnancy stage. A pregnancy stage may be marked by one or more characteristics of a female as the female carries a developing fetus. A pregnancy stage may include a preconception gestation phase where a female may be considering becoming pregnant but is not currently pregnant. During a preconception gestational phase 108, a female may aim to identify and modify one or more biomedical, behavioral, and/or social risks to the female's health or pregnancy outcome through prevention and management. For example, during a preconception gestational phase 108 a female may start to consume pre-natal vitamins to increase iron stores within her body. In yet another non-limiting example, during a preconception gestational phase 108 a female may gradually reduce and/or eliminate consumption of caffeine. A pregnancy stage may include a conception and implantation phase during which an egg meets up with a sperm cell and fertilization occurs. During a conception and implantation phase a fertilized egg moves to the lining of the uterus and implants to the uterine wall. In an embodiment, a conception and implantation phase may last anywhere from three to seven days. A pregnancy stage may include a first trimester phase which may last from week one through week twelve following conception and implantation. During a first trimester phase a developing embryo and subsequently fetus may begin to develop a heart, lungs, arms, legs, brain, spinal cord and nerves. A pregnancy stage may include a second trimester phase which may last from week thirteen through week twenty seven following conception and implantation. During a second trimester phase a developing embryo may develop eyebrows, eyelashes, fingernails, and neck. In addition, during a second trimester phase a fetus may sleep and wake on regular cycles and the fetus's brain may begin to rapidly develop. A pregnancy stage may include a third trimester phase which may last from week twenty eight to week forty following conception and implantation. During a third trimester phase a fetus may kick and stretch and may respond to light and sound such as music. During a third trimester phase a fetus may have fully mature lungs that are prepared to function on their own. A pregnancy stage may include a postpartum phase which may begin immediately after the birth of a child and last up to two years following the birth of the child. During the postpartum phase a female may nurse her child.

With continued reference to FIG. 1, computing device 104 calculates a gestational phase 108 by receiving a gestational datum 112. A "gestational datum," as used in this disclosure, is any data that is utilized to calculate a gestational phase 108. A gestational datum 112 may describe a user's due date which may be calculated by a medical professional such as a physician and/or nurse. For example, a physician may calculate a user's due date by adding 280 days to the first day of the user's last menstrual period. A gestational datum 112 may describe a user's conception date which may indicate a possible range of days during which a user's baby was conceived whether using artificial or natural methods. For example, a date of conception may reflect a range of days during which sexual intercourse may have led to conception. In yet another non-limiting example, a date of conception may reflect a date of an egg retrieval, a date of an embryo transfer, and/or a date of a blastocyst transfer if a fetus is conceived using artificial methods such as in vitro fertilization. A gestational datum 112 may describe a finding from an ultrasound scan such as a date that a baby's heartbeat is heard or a date when there is first fetal movement. A gestational datum 112 may describe one or more measurements obtained from an ultrasound such as a fundal height measurement or a uterus size measurement.

With continued reference to FIG. 1, one or more gestational datum 112 may be stored within user database 116. User database 116 may be implemented, without limitation, as a relational database, a key-value retrieval datastore such as a NOSQL database, or any other form or structure for use as a datastore that a person skilled in the art would recognize as suitable upon review of the entirety of this disclosure. In an embodiment, one or more gestational datum 112 may be obtained and stored within user database 116 from a remote device 120. Remote device 120 may include without limitation, a display in communication with computing device 104, where a display may include any display as described herein. Remote device 120 may include an additional computing device, such as a mobile device, laptop, desktop, computer, and the like. In an embodiment, a remote device 120 may be operated by a medical professional such as a physician or nurse who may record one or more gestational datum 112 during an appointment and/or consultation with a user and transmit them to computing device 104 to be stored within user database 116. A gestational datum 112 may be transmitted to computing device 104 utilizing any network methodology as described herein. In an embodiment, a remote device 120 may be operated by a user who may report to computing device 104 one or more gestational datum 112. For example, a user may enter on remote device 120 the date of her last menstrual period which may be transmitted to computing device 104 to be stored within user database 116.

With continued reference to FIG. 1, computing device 104 is configured to classify a gestational datum 112 to a gestational phase 108. Computing device 104 may classify a gestational datum 112 to a gestational phase 108 by generating a gestational classification algorithm 124. A "gestational classification algorithm," as used in this disclosure is any calculation and/or series of calculations that identify to which set of categories or "bins" a new observation or input belongs. Generating a gestational classification algorithm 124 may include generating a machine learning model using a classification algorithm. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Computing device 104 may utilize a gestational classification model that utilizes a gestational datum 112 as an input and outputs a gestational phase 108.

With continued reference to FIG. 1, computing device 104 is configured to generate a gestational phase label. A "gestational phase label," as used in this disclosure, is any textual, numerical, and/or symbolic data that identifies whether a gestational datum 112 belongs to a particular class or not, where a class may include any gestational phase 108. For example, a gestational phase label may indicate that currently a gestational datum 112 belongs to a second trimester gestational phase label and the gestational datum 112 does not belong to a preconception phase, a conception and implantation phase, a first trimester phase, a third trimester phase, and a postpartum phase.

With continued reference to FIG. 1, computing device 104 is configured to receive, from a remote device 120 operated by a user, a gestational inquiry 128. A "gestational inquiry," as used in this disclosure, is data containing any advice sought and/or question relating to any gestational phase. A gestational inquiry 128 may contain an inquiry related to any gestational phase including advice sought regarding medications including both prescription and non-prescription medications, vitamins, and supplements; pets; household products; fitness; chemicals; food consumption and food recommendations; alcohol consumption and alcohol recommendations; use of cosmetics; building materials such as paint; activities such as sports, leisure time activities; medical treatments; exposure to environmental toxins; travel including travel by cars, planes, trains, boats, and the like. A gestational inquiry 128 may contain advice sought regarding if a user can consume a particular medication while six months pregnant and if so at what dose. In yet another non-limiting example, a gestational inquiry 128 may contain a question regarding if it is safe for a user to have a certain pet live in the user's home throughout user's pregnancy. In yet another non-limiting example, a gestational inquiry 128 may seek advice about what household products are safe to use to clean user's house while pregnant. In yet another non-limiting example, a gestational inquiry 128 may question if a user can consume a particular food or meal while attempting to become pregnant. In yet another non-limiting example a gestational inquiry 128 may seek advice about what types of medical treatments are safe to be performed during a user's third trimester. In yet another non-limiting example, a gestational inquiry 128 may question if a user can use a sauna during the user's pregnancy and if so for how long. In yet another non-limiting example, a gestational inquiry 128 may contain an inquiry regarding any general retail product such as what linens are most suitable for a user or what mattress won't aggravate a user's sciatica problems. Computing device 104 receives a gestational inquiry 128 from a remote device 120 operated by a user. Gestational inquiry 128 may be transmitted from remote device 120 to computing device 104 utilizing any network methodology as described herein. In an embodiment, the gestational inquiry 128 may be extracted from the user using a chatbot as discussed in greater detail herein below.

With continued reference to FIG. 1, computing device 104 is configured to receive at an image catching device 132 located on the computing device 104 a wireless transmission from a remote device 120 containing a picture of the gestational inquiry 128. An "image catching device," as used in this disclosure, is any device capable of taking a picture and/or photograph of any product, item, and/or belonging associated with a gestational inquiry. Image catching device 132 may include a camera, mobile phone camera, scanner, or the like. For example, computing device 104 may receive at image catching device 132 a transmission from remote device 120 containing a picture of an over-the-counter medication such as a topical steroid cream. Computing device 104 may receive at image catching device 132 a wireless transmission from remote device 120 containing a picture of a uniform code commission barcode. For instance, and without limitation, user may be shopping at a grocery store and may photograph with an image catching device 132 contained within remote device 120 a photograph of a uniform code commission barcode located on a box of cereal. In an embodiment, image catching device 132 may be contained within remote device 120 and user may take a photograph of a uniform code commission barcode located on an item of clothing using remote device 120. In such an instance, the photograph of the uniform code commission barcode located on the item of clothing may be transmitted to computing device 104 utilizing any network transmission as described herein.

With continued reference to FIG. 1, computing device 104 is configured to receive from a remote device 120 a description of a gestational inquiry. In an embodiment, a description of a gestational inquiry may include a textual narrative describing a gestational inquiry 128. For example, a description of a gestational inquiry may describe that the user is currently experiencing increased back pain while sleeping that keeps the user up at night and the user would like to know what types of exercises will help to alleviate the user's back pain. In such an instance, computing device 104 separates a gestational inquiry 128 from a description of the gestational inquiry whereby the gestational inquiry 128 may be separated to produce "exercise to alleviate back pain." Computing device 104 may separate a gestational inquiry 128 from a description of a gestational inquiry utilizing a language processing module 136. Computing device 104 may separate a gestational inquiry 128 from a description of a gestational inquiry by removing any unnecessary information and/or words that may not be necessary and may contain additional information and/or peripheral details With continued reference to FIG. 1, language processing module 136 may be configured to extract one or more words from a description of a gestational inquiry. Language processing module 136 may include any hardware and/or software module. Language processing module 136 may be configured to extract, from one or more inputs, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module 136 may operate to produce a language processing model. Language processing model may include a program automatically generated by a computing device 104 and/or language processing module 136 to produce associations between one or more words extracted from at least a document and detect associations, including without limitation mathematical associations, between such words, and/or associations of extracted words with categories of gestational inquiries. Associations between language elements, where language elements include for purposes herein extracted words describing and/or including questions and/or advice sought relating to any gestational phase 108 may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of gestational inquiries. As a further example, statistical correlations and/or mathematical associations may include probabilistic formulas or relationships indicating a positive and/or negative association between at least an extracted word and/or a given category of gestational inquiry 128; positive or negative indication may include an indication that a given document is or is not indicating a particular category of gestational inquiry 128. For instance, and without limitation, a negative indication may be determined from a phrase such as "symptoms did not indicate greater pain at night," whereas a positive indication may be determined from a phrase such as "symptoms did indicate better pain control with exercise," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on a computing device 104, or the like.

Still referring to FIG. 1, language processing module 136 and/or a computing device 104 may generate a language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated.

In an alternative or additional approach, sequential tokens may be modeled as chains, serving as the observations in a Hidden Markov Model (HMM), HMMs as used herein are statistical models with inference algorithms that that may be applied to the models. In such models, a hidden state to be estimated may include an association between an extracted word category of a gestational inquiry 128. There may be a finite number of categories of gestational inquiries, to which an extracted word may pertain; an HMM inference algorithm, such as the forward-backward algorithm or the Viterbi algorithm, may be used to estimate the most likely discrete state given a word or sequence of words. Language processing module 136 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 136 may use a corpus of documents to generate associations between language elements in a language processing module 136, and a computing device 104 may then use such associations to analyze words extracted from one or more documents and determine that the one or more documents indicate significance of a category of gestational inquiries. In an embodiment, a computing device 104 may perform this analysis using a selected set of significant documents, such as documents identified by one or more experts as representing good science, good clinical analysis, or the like; experts may identify or enter such documents via a graphical user interface as described below, or may communicate identities of significant documents according to any other suitable method of electronic communication, or by providing such identity to other persons who may enter such identifications into a computing device 104. Documents may be entered into a computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, a computing device 104 may automatically obtain the document using such an identifier, for instance by submitting a request to a database or compendium of documents such as JSTOR as provided by Ithaka Harbors, Inc. of New York.

With continued reference to FIG. 1, computing device 104 is configured to classify a gestational inquiry 128 to an inquiry category 140. An "inquiry category," as used in this disclosure, is data categorizing a gestational inquiry 128 as having relevance to a particular topic. In an embodiment, an inquiry category 140 may indicate if a gestational inquiry 128 pertains to a medication for example, or if a gestational inquiry 128 pertains to fitness. In an embodiment, an inquiry category 140 may indicate one or more sub-categories that a gestational inquiry 128 may relate to. For instance and without limitation, an inquiry category 140 such as nutrition may be further broken down into sub-categories that include food, supplements, meal plans, individual ingredients, medical foods, absorption, assimilation, food preparation, specific diets, and the like. In yet another non-limiting example, an inquiry category 140 such as general retail may be further broken down into sub-categories that include video, music, electronics, clothing, shoes, jewelry, watches, groceries, games, computers, home, garden, tools, pet supplies, food, beauty, health, toys, kids, baby, handmade, sports, outdoors, automotive, industrial, and the like. An inquiry category 140 may contain information relating to any sub-categories that a gestational inquiry 128 may relate to.

With continued reference to FIG. 1, computing device 104 may classify a gestational inquiry 128 to an inquiry category 140 using a category classification algorithm 144. A "category classification algorithm," as used in this disclosure, is any calculation and/or series of calculations that identify to which set of categories or "bins" a new observation or input belongs. Generating a category classification algorithm 144 may include generating a machine learning model using a classification algorithm. Classification algorithm includes any of the classification algorithms as described above in more detail. In an embodiment, category classification algorithm 144 includes any algorithm suitable for use as gestational classification algorithm 124. Category classification algorithm 144 utilizes a gestational inquiry 128 as an input and outputs an inquiry category 140.

With continued reference to FIG. 1, computing device 104 selects a gestational machine-learning model as a function of an inquiry category 140. In an embodiment, one or more machine-learning models may be previously calculated and loaded into system 100. One or more machine-learning models may be stored in a computing device database 148. Computing device database 148 includes any data structure suitable for use as user database 116. In an embodiment, one or more machine-learning models may be intended for one or more inquiry categories. Computing device 104 may locate a machine-learning model intended for a matching inquiry category 140. For instance and without limitation, computing device 104 may classify a gestational inquiry 128 to an inquiry category 140 such as vitamins. In such an instance, computing device 104 may locate within computing device database 148 a machine-learning model generated for vitamins. In yet another non-limiting example, computing device 104 may classify a gestational inquiry to an inquiry category 140 such as fitness. In such an instance, computing device 104 may locate within computing device database 148 a machine-learning model generated for fitness. In an embodiment, one or more machine-learning algorithms may be organized within computing device database 148 by inquiry category 140 and further organized by one or more sub-categories.

With continued reference to FIG. 1, computing device 104 is configured to generate a gestational machine-learning model 152. A "gestational machine-learning model," as used in this disclosure, is a machine-learning model that utilizes a gestational phase label and a user biological extraction 156 as an input and outputs gestational eligibility labels. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 1, a machine learning process, also referred to as a machine-learning algorithm, is a process that automatedly uses training data and/or a training set as described above to generate an algorithm that will be performed by a computing device 104 and/or module to produce outputs given data provided as inputs; this is in contrast to a non-machine learning software program where the commands to be executed are determined in advance by a user and written in a programming language.

Continuing to refer to FIG. 1, machine-learning algorithms may be implemented using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure, Still referring to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised machine-learning process may include a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

With continued reference to FIG. 1, supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like. Unsupervised machine-learning algorithms may include, without limitation, clustering algorithms and/or cluster analysis processes, such as without limitation hierarchical clustering, centroid clustering, distribution clustering, clustering using density models, subspace models, group models, graph-based models, signed graph models, neural models, or the like. Unsupervised learning may be performed by neural networks and/or deep learning protocols as described above.

With continued reference to FIG. 1, a "biological extraction," as used in this disclosure, contains at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function, and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 136 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation, any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge, and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides* vulgates', *Bacteroides-Prevotella, Barnesiella* species, *Bifidobacterium* longarm, *Bifidobacterium* species, Butyrivbrio *crossotus, Clostridium* species, Collinsella aerofaciens, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, Methanobrevibacter *smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, generating gestational machine-learning model 152 includes receiving gestational training data 160. "Gestational training data," as used in this disclosure, is training data that includes a plurality of gestational phase labels and biological extraction 156 and correlated gestational eligibility. "Training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 outputs a plurality of gestational eligibility labels 164 for gestational inquiries related to an inquiry category 140 utilizing the gestational machine-learning model 152. A "gestational eligibility label," as used in this disclosure, is data containing an indication of either a positive or negative effect on a user's body based on the user's gestational phase 108 and the user's constitution as indicated by the user's biological extraction 156. A positive effect includes a gestational inquiry 128 that will not cause harm to the user and/or the user's fetus. A negative effect includes a gestational inquiry 128 that will cause harm to the user and/or the user's fetus. Computing device 104 may generate a plurality of gestational eligibility labels for gestational inquiries related to an inquiry category 140. For instance and without limitation, a gestational inquiry 128 may contain a question asking if the user can travel to Venezuela, and where the user is currently twenty two months pregnant and currently in the second trimester gestational phase 108. In such an instance, computing device 104 may output a plurality of gestational eligibility label 164 for other areas of travel such as a first gestational eligibility label 164 for travel to Brazil, a second gestational eligibility label 164 for travel to India, a third gestational eligibility label 164 for travel to California, and a fourth gestational eligibility label 164 for travel to Russia. In embodiment, computing device 104 may be configured to assign a gestational eligibility label to a gestational target 168 or a gestational suggestion.

With continued reference to FIG. 1, computing device 104 is configured to determine utilizing the gestational machine-learning model 152 the gestational eligibility of the gestational inquiry 128. "Gestational eligibility," as used in this disclosure, is data including any textual, numerical, and/or symbolic data indicating whether a gestational inquiry is safe and/or tolerated by a user during one or more gestational phases. In an embodiment, computing device 104 may determine that a gestational inquiry 128 is suitable for a user based on the user's current gestational phase 108. A "suitable" gestational inquiry, as used in this disclosure, is a gestational inquiry that that will have a positive effect on a user. A gestational inquiry 128 may be suitable for a user when a gestational eligibility label indicates that the gestational inquiry 128 will have a positive effect as described above in more detail. A gestational inquiry 128 may not be suitable for a user when a gestational eligibility label 164 indicates that the gestational inquiry 128 will have a negative effect as described above in more detail. Computing device 104 may determine the eligibility of a gestational inquiry 128 for subsequent gestational phase 108 or gestational phase 108 that occur after the current gestational phase 108. A current gestational phase 108 includes any gestational phase 108 that the user is experiencing at the present moment. For instance and without limitation, computing device 104 may determine that a shampoo is suitable for a user who is currently in the first trimester gestational phase 108. In such an instance, computing device 104 may determine the suitability of the same shampoo for the user in the second trimester, the third trimester, and a postpartum phase. In embodiment, computing device 104 may be configured to determine the gestational eligibility label to a gestational target 168 or a gestational suggestion.

With continued reference to FIG. 1, computing device 104 may determine that a gestational inquiry 128 is suitable for a user and initiate a limitation on a gestational inquiry. A "limitation on a gestational inquiry" as used in this disclosure, is data describing a restriction placed on a gestational inquiry 128. A restriction may indicate a certain maximum number of times a gestational inquiry 128 may be practiced, such as a trip to a tanning salon which may be performed no more than one time per month while the user is breastfeeding and in the postpartum phase. In yet another non-limiting example, a restriction may describe a modification of a gestational inquiry 128. For example, a restriction may indicate that a user who is in the first trimester may engage in physical activity but only if the user's heart rate stays below 100 beats per minute. If the user's heart rate rises above 100 beats per minute, then the user must stop any physical activity that the user is currently engaged in. A restriction may indicate a maximum quantity of a gestational inquiry 128. For example, a restriction may indicate that no more than 4000 mg of acetaminophen may be consumed by the user in any one day during the third trimester.

With continued reference to FIG. 1, computing device 104 may determine that a gestational inquiry 128 is not suitable for a user such as when a gestational eligibility label 164 contains a negative effect. In such an instance, computing device 104 identifies suitable gestational inquiries related to an inquiry category 140. For example, computing device 104 may identify gestational eligibility labels generated for gestational inquiries related to the inquiry category 140 that contain a positive effect. Computing device 104 may recommend suitable gestational inquiries related to the inquiry category 140 as a function of the user biological extraction 156 and the user gestational phase 108.

With continued reference to FIG. 1, computing device 104 may determine that a gestational inquiry 128 is not suitable for a first gestational phase 108 where a first gestational phase 108 includes any gestational phase 108 that occurs before a second gestational phase 108. A second gestational phase 108 includes any gestational phase 108 that occurs after a first gestational phase 108. Computing device 104 may determine that the gestational inquiry 128 is suitable for the second gestational phase 108. For instance and without limitation, computing device 104 may determine that hair dye is not suitable for a user in the first trimester or the second trimester but is suitable in the third trimester and in the postpartum phase.

With continued reference to FIG. 1, computing device 104 may be configured to create one or more gestational targets 168 as a function of the gestational inquiry 128. As used in the current disclosure, a "gestational target" is a health-based goal for a pregnant person. Gestational targets 168 for a pregnant person are specific objectives and aspirations aimed at promoting and maintaining optimal physical, mental, and emotional well-being during pregnancy. Gestational targets 168 may be set according to each gestational phase 108. These goals are tailored to support the health of both the mother and the developing baby. Gestational targets 168 may be defined objectives that focus on achieving and maintaining a healthy lifestyle, balanced nutrition, appropriate physical activity, regular medical check-ups, adequate rest, and effective stress management to ensure the well-being of the pregnant individual and the developing fetus. These goals may encompass aspects such as diet, exercise, prenatal care, mental health, and overall healthy habits to support a successful pregnancy and a healthy birth outcome. Examples of gestational targets 168 may include dietary goals, fitness goals, check-in goals, hydration goals, rest goals, stress management goals, substance abuse goals, education goals, labor and delivery goals, hygiene goals, and the like. In some cases, the computing device may use a sensor such as a wearable device to monitor the user as they set out to achieve their goals. The sensor may be configured to collect information from the user, including heart rate, sleep patterns, sleep cycles, caloric intake, number of calories burned, hydration, and the like. This information will be paired with the demographics, medical history, current health status, lifestyle choices, preferences, of the user to set and monitor goals for the user. Computing device 104 may implement algorithms, such as target machine learning model, that considers the user's biological extraction, desired health outcomes according to gestational inquiry 128, and reference guidelines to set achievable, measurable, and time-bound gestational targets 168. In some embodiments, computing device 104 may generate gestational targets 168 using a lookup table or querying a database. In some embodiments, gestational targets 168 may be shared with a medical professional automatically. In some embodiments, gestational targets 168 may be communicated with a remote device 120 of a medical professional. This may be done via email, text message, push notifications, a shared platform (i.e. a computer application), and the like. The medical professional may modify, alter, and/or veto the proposed gestational targets 168 according to their medical judgement.

With continued reference to FIG. 1, computing device 104 may identify a nutrient threshold according to the dietary goals of the user. Dietary goals may include assigning the user a nutrient threshold according to the biological extraction of the user. As used in the current disclosure, a "nutrient threshold" refers to the specific recommended or optimal amount of essential nutrients that a pregnant person should aim to consume during pregnancy. These thresholds ensure that the mother and developing baby receive adequate nutrition critical for growth, development, and overall health. Nutrient thresholds vary based on factors such as stage of pregnancy, individual health status, age, weight, and specific dietary needs. Examples of nutrient thresholds may include thresholds associated with the user's intake of Folic Acid, Iron, Calcium, Omega-3 fatty acids, Protein, Vitamin D, Vitamin B12, Vitamin C, Vitamin A. In a non-limiting example, a nutrient threshold may require a user to consume at least 600-800 micrograms (mcg) of folic acid per day. In another non-limiting example, a nutrient threshold may require a user to consume approximately 27-30 milligrams (mg) of iron per day and/or about 200-300 milligrams (mg) of DHA per day. Nutrient thresholds may be assigned to the user according to the biological extraction and gestational phase of the user. Computing device 104 may additionally refer to established guidelines and recommendations for nutrient thresholds during pregnancy, often provided by reputable health organizations or government health agencies. Examples include the Dietary Guidelines for Americans and specific guidelines for pregnancy issued by organizations like the World Health Organization (WHO) or the Institute of Medicine (IOM). When tailoring the nutrient threshold to the user a computing device 104 may account for various variables that may influence nutrient requirements, such as the trimester of pregnancy, any existing medical conditions, multiple pregnancies (e.g., twins, triplets, etc.), and specific dietary needs or restrictions. The processor may then tailor the calculated nutrient thresholds to the individual's circumstances, ensuring the recommendations are realistic, achievable, and safe based on their biological extraction.

With continued reference to FIG. 1, a gestational target 168 may contain one or more gestational suggestions 172. As used in the current disclosure, a "gestational suggestion" is recommendation comprised of a step or set of steps to support the achievement of a particular health or wellness goal. These suggestions may be tailored to each user according to the user's gestational inquiry, biological extraction, and the stated gestational target 168. A user's gestational inquiry may provide identify an area in which a user would like to set a gestational target 168. Whereas the gestational target 168 may be a tailored health goal for the pregnant person. A gestational suggestion 172 may include a detailed roadmap comprised of steps and sub-steps of the gestational target 168. In a non-limiting example, if the gestational target 168 comprises one or more daily nutrient thresholds. A gestational suggestion 172 may include an itemized list of foods, meals, snacks, and the like that would allow the user to achieve their nutrient thresholds. In some cases, a gestational suggestion 172 may include a purchase list for the user. As used in the current disclosure, a "purchase list" is an itemized list of items which are required to achieve a gestational target 168. A purchase list may include a grocery list, whereas the grocery list identifies food items needed by the user in order to cook a meal that satisfies a dietary goal of the user. A gestational suggestion 172 may additionally include one or more recipes associated with the grocery list to provide the user with clear food preparation instructions. A purchase list may additionally include items such as hygiene items, vitamins, neonatal care items, fitness equipment, medicines, child care items, and the like. A Gestational suggestion 172 may address the unique needs and circumstances of a pregnant individual and are aimed at promoting a healthy pregnancy and optimal development of the baby. These gestational suggestions 172 aim to provide actionable advice and tips, guiding the pregnant individual toward achieving their health goals and ensuring a healthy and successful pregnancy. Gestational suggestions 172 may be provided to the user for each gestational target 168 assigned to the user. New gestational suggestions 172 may be provided to the user each day, week, month, trimester, and the like. In a non-limiting example, a user may have a gestational target 168 centered around the pregnant persons fitness. A gestational suggestion 172 may include suggestions that the pregnant person take 10,000 steps per day in their first trimester. In an additional example, a user may have a gestational target 168 associated with mental health of the pregnant person. The gestational suggestion 172 may include a suggestion to meet with a mental health professional once per week.

With continued reference to FIG. 1, a gestational suggestion 172 may include a fitness suggestion. As used in the current disclosure, a "fitness suggestion" is a gestational suggestion 172 related to fitness of the user. A fitness suggestion may be tailored to promote physical activity and encourage a healthy level of exercise suitable for each trimester. A fitness suggestion may include a customized exercise plan. In some cases, a fitness suggestion may include a recommendation to consult a healthcare provider or a fitness instructor. Processor 104 may match the user to a fitness instructor as a function of specific the fitness suggestion. In a non-limiting example, if the fitness suggestion prompts a user to participate in yoga, then processor 104 may pair the user with yoga instructors within the users geographic area. Pairing of the user and the fitness instructor may include organizing a chatroom, video call, audio call, instant messenger, text message, email, and the like between the fitness instructor and the user. Pairing the user and the fitness instructor may additionally include an exchange of contact information between the user and the fitness instructor. A list of fitness instructors may be stored on a database, wherein processor 104 queries the database to find one or more fitness instructors who are suitable for the user according to the fitness suggestion, geographic location, price range, and gestational phase. Fitness suggestions may include exercise recommendations. This may include activities like walking, swimming, stationary cycling, low-impact aerobics, and the like. Fitness suggestions may be modified through the term of the pregnancy according to user feedback, medical professional recommendation, standardized guidelines, changes to the user's biological extraction, and the like.

With continued reference to FIG. 1, a gestational suggestion 172 may include a dietary suggestion. As used in the current disclosure, a "dietary suggestion" is a gestational suggestion 172 related to diet of the user. A dietary suggestion may include the creation of a personalized eating plan based on user specific needs and preferences. Alternatively, a dietary suggestion may include a recommendation of a food item for a pregnant person. A dietary suggestion may be modified according to a user's dietary restrictions, user preferences, biological extraction 156, and the like. A meal plan may include a plan for balanced meals that include a variety of fruits, vegetables, whole grains, lean proteins, dairy or dairy alternatives, and the like. A dietary suggestion may aim to guide the pregnant individual in making informed dietary choices that align with their nutritional needs during pregnancy. It emphasizes a balanced and nutritious diet to support a healthy pregnancy and ensure the best possible outcomes for both the expectant mother and the baby. A dietary suggestion may be generated as a function of a nutrient threshold assigned to the current user. Dietary suggestion may include suggestions to consume various vitamins and other over the counter neonatal products. Dietary suggestions may be modified or altered according to a dietary input by the user. A dietary input may be created using a camera or other sensor to scan the nutritional facts located on packaged food. Dietary inputs also may use weights/volume of uncooked foods to determine the nutritional value of the food. In an embodiment, dietary inputs may be submitted to the system and the system may display to the user how consumption of the food item will affect the user's meal plan. If the user consumes the food item the remaining dietary suggestions or meals for the day may be altered. In a non-limiting example, if a user submits a dietary input for a food item that is high in sugar the remaining dietary suggestions may be altered to balance the users sugar intake in accordance with the user's nutritional threshold. In an embodiment, the nutritional threshold may be received from a database, a medical professional, and the like. In some cases, processor 104 may generate a nutritional threshold based on the gestational phase, demographic factors, the user's biological extraction 156, and the like. Processor 104 may compare the aforementioned data points to known medical standards for neonatal nutrition to generate the nutritional threshold. In some cases, the nutritional threshold may be a predetermined based upon one or more of the aforementioned data points.

With continued reference to FIG. 1, a dietary suggestion may include a recommendation to consult a dietitian. This may include a dietitian specializing in prenatal nutrition. Processor 104 may match the user to a dietitian as a function of specific the dietary suggestion. In a non-limiting example, if the dietary suggestion prompts a user to consume a neonatal vitamin, then processor 104 may pair the user with dietitian who has knowledge of the neonatal vitamin. The dietitian may inform the user about the risks and benefits of the dietary suggestion. In some cases, the dietitian may modify or alter the dietary suggestion to be more tailored to the user's needs. Pairing of the user and the dietitian may include organizing a chatroom, video call, audio call, instant messenger, text message, email, and the like between the dietitian and the user. Pairing the user and the dietitian may additionally include an exchange of contact information between the user and the dietitian. A list of dietitians may be stored on a database, wherein processor 104 queries the database to find one or more dietitians who are suitable for the user according to the dietary suggestion, geographic location, price range, availability, gestational phase, and the like.

With continued reference to FIG. 1, computing device 104 may generate one or more motivational messages associated with the gestational target. As used in the current disclosure, a "motivational message" is an inspiring or uplifting communication that aims to encourage, empower, or energize the user. The motivational message may encourage the user to take positive action, face challenges, and pursue their goals with determination and enthusiasm. It often conveys hope, resilience, belief in oneself, and the potential for growth and success. The motivational message may be tailored to the current gestational target 168 of the user. In an non-limiting example, a user may be provided with a motivational message after completion of a mile stone to encourage them to continue to keep striving. In some cases, the motivational message may include religious undertones such as bible verses and the like. A non-limiting example of a motivational message may include messages like "You are going to be a great parent;" "You have been crushing it this past week;" "You are close to your daily goal so do not quit now;" and the like. Motivational messages may be generated as an output of the target machine learning model or the LLM as mentioned in greater detail herein below. As a non-limiting example, an LLM may receive a gestational target as input and output a motivational message. In some embodiments, this LLM may be trained on training data comprising a plurality of gestational targets correlated to a plurality of motivational messages.

With continued reference to FIG. 1, computing device 104 may generate gestational targets 168 using a target machine-learning model. As used in the current disclosure, a "target machine-learning model" is a machine-learning model that is configured to generate gestational targets 168. A target machine-learning model may be consistent with the machine-learning model described below in FIG. 5. Inputs to the target machine-learning model may include gestational phase 108, gestational datum 112, gestational inquiry 128, inquiry categories 140, biological extractions 156, examples of gestational targets 168, and the like. Inputs to the target machine-learning model may also include the outputs of the gestational machine learning model 152 or any other machine learning model/classifier mentioned herein. Outputs to the target machine-learning model may include gestational targets 168 tailored to the gestational inquiries 128 and biological extraction 156 of the user. Target training data may include a plurality of data entries containing a plurality of inputs that are correlated to a plurality of outputs for training a processor by a machine-learning process. In an embodiment, target training data may include a plurality of gestational inquiry 128 and biological extractions 156 as inputs correlated to examples of gestational targets 168 as outputs. Target training data may be received from a database. Target training data may additionally contain data from pregnant people in the same gestational phase 108 as the user. This may include biological extractions 156 and gestational inquires 128. In an additional embodiment, the target machine-learning model may be specifically trained using training data which includes biological extractions from users within the same gestational phase 108 as the current user as inputs correlated to examples of gestational targets 168 as outputs. Target training data may contain information about gestational phase 108, gestational datum 112, gestational inquiry 128, inquiry categories 140, biological extractions 156, examples of gestational targets 168, and the like. In an embodiment, target training data may be iteratively updated as a function of the input and output results of past target machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, machine learning plays a crucial role in enhancing the function of software for generating a target machine-learning model. This may include identifying patterns within the biological extraction 156 that lead to the establishment of gestational targets 168. By analyzing vast amounts of data related to biological extractions 156, machine learning algorithms can identify patterns, correlations, and dependencies that contribute to a generating the target machine-learning model. These algorithms can extract valuable insights from the user's biological extraction 156. By applying machine learning techniques, the software can generate the target machine-learning model extremely accurately. Machine learning models may enable the software to learn from past collaborative experiences of the entities and iteratively improve its training data over time.

With continued reference to FIG. 1, computing device 104 may be configured to update the training data of the target machine-learning model using user inputs. A target machine-learning model may use user input to update its training data, thereby improving its performance and accuracy. In embodiments, the target machine-learning model may be iteratively updated using input and output results of the target machine-learning model. The target machine-learning model may then be iteratively retrained using the updated machine-learning model. For instance, and without limitation, target machine-learning model may be trained using first training data from, for example, and without limitation, training data from a user input or database. The target machine-learning model may then be updated by using previous inputs and outputs from the target machine-learning model as second training data to then train a second machine learning model. This process of updating the target machine-learning model may be continuously done to improve the speed and accuracy of the target machine-learning model. When users interact with the software, their actions, preferences, and feedback provide valuable information that can be used to refine and enhance the model. This user input is collected and incorporated into the training data, allowing the machine learning model to learn from real-world interactions and adapt its predictions accordingly. By continually incorporating user input, the model becomes more responsive to user needs and preferences, capturing evolving trends and patterns. This iterative process of updating the training data with user input enables the machine learning model to deliver more personalized and relevant results, ultimately enhancing the overall user experience. The discussion within this paragraph may apply to both the target machine-learning model or any other machine-learning models/classifiers discussed herein.

Incorporating the user feedback may include updating the training data by removing or adding correlations of user data to a path or resources as indicated by the feedback. Any machine-learning model as described herein may have the training data updated based on such feedback or data gathered using a web crawler as described above. For example, correlations in training data may be based on outdated information wherein, a web crawler may update such correlations based on more recent resources and information.

With continued reference to FIG. 1, computing device 104 may use user feedback to train the machine-learning models and/or classifiers described above. For example, target machine-learning model may be trained using past inputs and outputs of target machine-learning model. In some embodiments, if user feedback indicates that an output of machine-learning models and/or classifiers was "bad," then that output and the corresponding input may be removed from training data used to train classifier, and/or may be replaced with a value entered by, e.g., another value that represents an ideal output given the input the machine-learning models and/or classifiers originally received, permitting use in retraining, and adding to training data; in either case, target machine-learning model may be retrained with modified training data as described in further detail below. In some embodiments, training data of target machine-learning model may include user feedback.

With continued reference to FIG. 1, in some embodiments, an accuracy score may be calculated for target machine-learning model using user feedback. For the purposes of this disclosure, "accuracy score," is a numerical value concerning the accuracy of a machine-learning model. For example, the accuracy/quality of the outputted target machine-learning model may be averaged to determine an accuracy score. In some embodiments, an accuracy score may be determined for the viability of the gestational target 168. Accuracy score or another score as described above may indicate a degree of retraining needed for a machine-learning model such as a classifier; computing device 104 may perform a larger number of retraining cycles for a higher number (or lower number, depending on a numerical interpretation used), and/or may collect more training data for such retraining. The discussion within this paragraph and the paragraphs preceding this paragraph may apply to both the target machine-learning model or any other machine-learning model/classifier mentioned herein.

With continued reference to FIG. 1, in one or more embodiments, computing device 104 may implement one or more aspects of "generative artificial intelligence (AI)," a type of AI that uses machine learning algorithms to create, establish, or otherwise generate data such as, without limitation, gestational targets 168, gestational reports, and/or the like in any data structure as described herein (e.g., text, image, video, audio, among others) that is similar to one or more provided training examples. In an embodiment, machine learning module described herein may generate one or more generative machine learning models that are trained on one or more set of event training data and/or report training data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, "generative models" refers to statistical models of the joint probability distribution $P(X,Y)$ on a given observable variable x, representing features or data that can be directly measured or observed (e.g. biological extraction 156) and target variable y, representing the outcomes or labels that one or more generative models aims to predict or generate (e.g., a gestational target 168). In some cases, generative models may rely on Bayes theorem to find joint probability; for instance, and without limitation, Naïve Bayes classifiers may be employed by computing device 104 to categorize input data such as, without limitation the biological extraction 156 into one or more gestational targets 168.

In a non-limiting example, and still referring to FIG. 1, one or more generative machine learning models may include one or more Naïve Bayes classifiers generated, by computing device 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X,Y) over observable variables X and target variable Y. In an embodiment, Naïve Bayes classifier may be configured to make an assumption that the features X are conditionally independent given class label Y, allowing generative model to estimate the joint distribution as P(X,Y)=P(Y)ΠiP(Xi|Y), wherein P(Y) may be the prior probability of the class, and P(X_i|Y) is the conditional probability of each feature given the class. One or more generative machine learning models containing Naïve Bayes classifiers may be trained on labeled training data, estimating conditional probabilities P(X_i|Y) and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature X_i, sample at least a value according to conditional distribution P(X_i|y). Sampled feature values may then be combined to form one or more new data instance with selected class label y. In a non-limiting example, one or more generative machine learning models may include one or more Naïve Bayes classifiers to generate new examples of a comprehensive reports and/or a user scores based on inputs as described herein, wherein the models may be trained using training data containing a plurality of features, and/or the like as input correlated to a plurality of labeled classes.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 2.

With continued reference to FIG. 1, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 2 to distinguish between different categories, or states e.g., TRUE vs. FALSE within the context of generated data such as, without limitations, a comprehensive report and/or a user score, and/or the like. In some cases, computing device 104 may implement one or more classification algorithms such as, without limitation, Support Vector Machines (SVM), Logistic Regression, Decision Trees, and/or the like to define decision boundaries.

With continued reference to FIG. 1, processor 104 is configured to generate a gestational report 176 as a function of the gestational target 168. As used in the current disclosure, a "gestational report" is a document that provides detailed information about an individual's progress in a gestational target 168. Gestational reports 176 may contain a variety of information associated with the user's gestational target 168. A gestational report 176 generated as a function of gestational targets 168 may be used to monitor, evaluate, and guide the pregnant individual in achieving a healthy and successful pregnancy while addressing specific health goals and objectives. The report serves as a tool for both the individual and healthcare professionals to track progress and make informed decisions throughout the gestational period. In some cases, the gestational report 176 may be iteratively shared with the user's chosen medical professional. This may be done to provide the medical professional with continuous updates regarding the pregnant person's health. Gestational reports 176 may include information such as personal information, past/present gestational targets 168, baseline health metrics, a user specific identifier, and the like. In an embodiment, a gestational report 176 may contain information associated with a user's progress towards their dietary goals. This may include a summary of dietary goals, including recommended nutrient intake, calorie goals, dietary adjustments, and the like. Additionally, the report may contain information on the individual's dietary habits, adherence to dietary recommendations, and any challenges faced in meeting the goals. The gestational targets 168 may be updated according to the user adherence or non-compliance with the gestational target 168. In another non-limiting example, a gestational report 176 may detail the prescribed exercise regimen associated with the fitness goals of the user, including types of exercises, frequency, and duration. The report may contain information on the individual's participation in exercise routines, progress, and adjustments made to the fitness plan. In an additional non-limiting example, the gestational report may present stress management goals, relaxation techniques, and mindfulness practices recommended during pregnancy. The report may contain information documenting the individual's efforts in managing stress, incorporating relaxation practices, and overall emotional well-being. Gestational reports 176 may issue warnings to the user if harmful behaviors are detected. In an embodiment, emphasize the importance of avoiding harmful substances and adhering to prescribed medications under medical supervision. The gestational report may include a record of the individual's compliance with substance avoidance and medication guidelines.

With continued reference to FIG. 1, processor 104 may generate a gestational report 176 using a report machine-learning model. As used in the current disclosure, a "report machine-learning model" is a machine-learning model that is configured to generate a gestational report 176. Report machine-learning model may be consistent with the machine-learning model described below in FIG. 5. Inputs to the report machine-learning model may include gestational phase 108, gestational datum 112, gestational inquiry 128, inquiry categories 140, biological extractions 156, gestational targets 168, gestational suggestions 172, examples of gestational reports 176, and the like. Outputs to the report machine-learning model may include gestational report tailored to the one or more gestational targets 168. report training data may include a plurality of data entries containing a plurality of inputs that are correlated to a plurality of outputs for training a processor by a machine-learning process. In an embodiment, report training data may include a plurality of one or more gestational targets 168 correlated to examples of gestational reports 176. report training data may be received from database. report training data may contain information about the gestational phase 108, gestational datum 112, gestational inquiry 128, inquiry categories 140, biological extractions 156, gestational targets 168, gestational suggestions 172, dietary suggestions, fitness suggestions, purchases list, examples of gestational reports 176, and the like. In an embodiment, report training data may be iteratively updated as a function of the input and output results of past report machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

Still referring to FIG. 1, a report machine-learning model may include a large language model (LLM). A LLM may be a type of generative machine-learning model, as described above. A "large language model," as used herein, is a deep learning algorithm that can recognize, summarize, translate, predict and/or generate text and other content based on knowledge gained from massive datasets. Large language model may be trained on large sets of data; for example, training sets may include greater than 1 million words. Training sets may be drawn from diverse sets of data such as, as non-limiting examples, novels, blog posts, articles, emails, medical records, medical textbooks, medical research, medical journals, and the like. In some embodiments, training sets may include a variety of subject matters, such as, as nonlimiting examples, user specific medical records, biological extractions, fitness records, dietary records, user communications, and the like. In some embodiments, training sets of LLM may include examples of gestational reports. In some embodiments, training sets of LLM may include information from one or more public or private databases. As a non-limiting example, training sets may include databases associated with an entity.

With continued reference to FIG. 1, in some embodiments, LLM may be generally trained. For the purposes of this disclosure, "generally trained" means that LLM is trained on a general training set comprising a variety of subject matters, data sets, and fields. In some embodiments, LLM may be initially generally trained. In some embodiments, for the purposes of this disclosure, LLM may be specifically trained. For the purposes of this disclosure, "specifically trained" means that LLM is trained on a specific training set, wherein the specific training set includes data including specific correlations for LLM to learn. As a non-limiting example, LLM may be generally trained on a general training set, then specifically trained on a specific training set. As a non-limiting example, specific training set may include examples of comprehensive reports. As a non-limiting example, specific training set may include scholastic works. As a non-limiting example, specific training set may include information from a database. As a non-limiting example, specific training set may include text related to the users such as biological extractions 156, user medical records, gestational targets 168, previous versions of gestational reports, and the like.

With continued reference to FIG. 1, LLM, in some embodiments, may include Generative Pretrained Transformer (GPT), GPT-2, GPT-3, GPT-4, and the like. GPT, GPT-2, GPT-3, and GPT-4 are products of Open AI Inc., of San Francisco, CA. LLM may include a text prediction based algorithm configured to receive an article and apply a probability distribution to the words already typed in a sentence to work out the most likely word to come next in augmented articles. For example, if the words already typed are "Nice to meet", then it is highly likely that the word "you" will come next. LLM may output such predictions by ranking words by likelihood or a prompt parameter. For the example given above, the LLM may score "you" as the most likely, "your" as the next most likely, "his" or "her" next, and the like. LLM may include an encoder component and a decoder component.

Still referring to FIG. 1, LLM may include a transformer architecture. In some embodiments, encoder component of LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, an attention mechanism may represent an improvement over a limitation of the Encoder-Decoder model. The encoder-decider model encodes the input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, LLM may predict the next word by searching for a set of position in a source sentence where the most relevant information is concentrated. LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, an attention mechanism may include generalized attention self-attention, multi-head attention, additive attention, global attention, and the like. In generalized attention, when a sequence of words or an image is fed to LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, LLM may pick up particular parts at different positions in the input sequence and over time compute an initial composition of the output sequence. In multi-head attention, LLM may include a transformer model of an attention mechanism. Attention mechanisms, as described above, may provide context for any position in the input sequence. For example, if the input data is a natural language sentence, the transformer does not have to process one word at a time. In multi-head attention, computations by LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), LLM may make use of attention alignment scores based on a number of factors. These alignment scores may be calculated at different points in a neural network. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, LLM may either attend to all source words or predict the target sentence, thereby attending to a smaller subset of words.

With continued reference to FIG. 1, multi-headed attention in encoder may apply a specific attention mechanism called self-attention. Self-attention allows the models to associate each word in the input, to other words. So, as a non-limiting example, the LLM may learn to associate the word "you", with "how" and "are". It's also possible that LLM learns that words structured in this pattern are typically a question and to respond appropriately. In some embodiments, to achieve self-attention, input may be fed into three distinct fully connected layers to create query, key, and value vectors. The query, key, and value vectors maybe fed through a linear layer; then, the query and key vectors may be multiplies using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With continued reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am", decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that class will be of size 10,000. The output of this classifier may be fed into a softmax layer which may serve to produce probability scores between zero and one. The index may be taken of the highest probability score in order to determine a predicted word.

With continued reference to FIG. 1, decoder may take this output and add it to the decoder inputs. Decoder may continue decoding until a token is predicted. Decoder may stop decoding once it predicts an end token.

With continued reference to FIG. 1, in some embodiment, decoder may be stacked N layers high, with each layer taking in inputs from the encoder and layers before it. Stacking layers may allow LLM to learn to extract and focus on different combinations of attention from its attention heads.

With continued reference to FIG. 1, LLM may receive an input. Input may include a string of one or more characters. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. Query may include, for example a question asking for a status update regarding a to-do list. In some embodiments, input may include a gestational target 168 and gestational suggestions 172 associated with the user.

With continued reference to FIG. 1, LLM may generate an output. In some embodiments, LLM may include multiple sets of transformer architecture as described above. Output may include a textual output. A "textual output," for the purposes of this disclosure is an output comprising a string of one or more characters. Textual output may include, for example, a comprehensive report. In some embodiments, textual output may include a phrase or sentence identifying the status of a user query. In some embodiments, textual output may include a sentence or plurality of sentences describing a response to a user query. As a non-limiting examples, this may include, restrictions, timing, advice, dangers, benefits, and the like.

With continued reference to FIG. 1, processor 104 may pair the current user with other users within the same gestational phase 108. Processor 104, in some embodiments, may generate a chatroom. A "chatroom," is a form of synchronous or asynchronous conferencing allowing a selected set of users to exchange textual, photographic, or auditory messages. Processor may allow each user to interact with each other using a chatroom, audio call, video call, instant messenger, and the like. This fosters a collaborative environment where users can share experiences, insights, and support, enhancing their journey within the specific gestational phase 108. Users are given the opportunity to exchange experiences, knowledge, and emotional support, whether it's expectant parents, individuals undergoing similar medical treatments, or people facing comparable life stages. This feature not only enriches the user experience but also promotes a sense of belonging and camaraderie within the platform, ultimately strengthening the community and its users' overall well-being.

Figure 2:
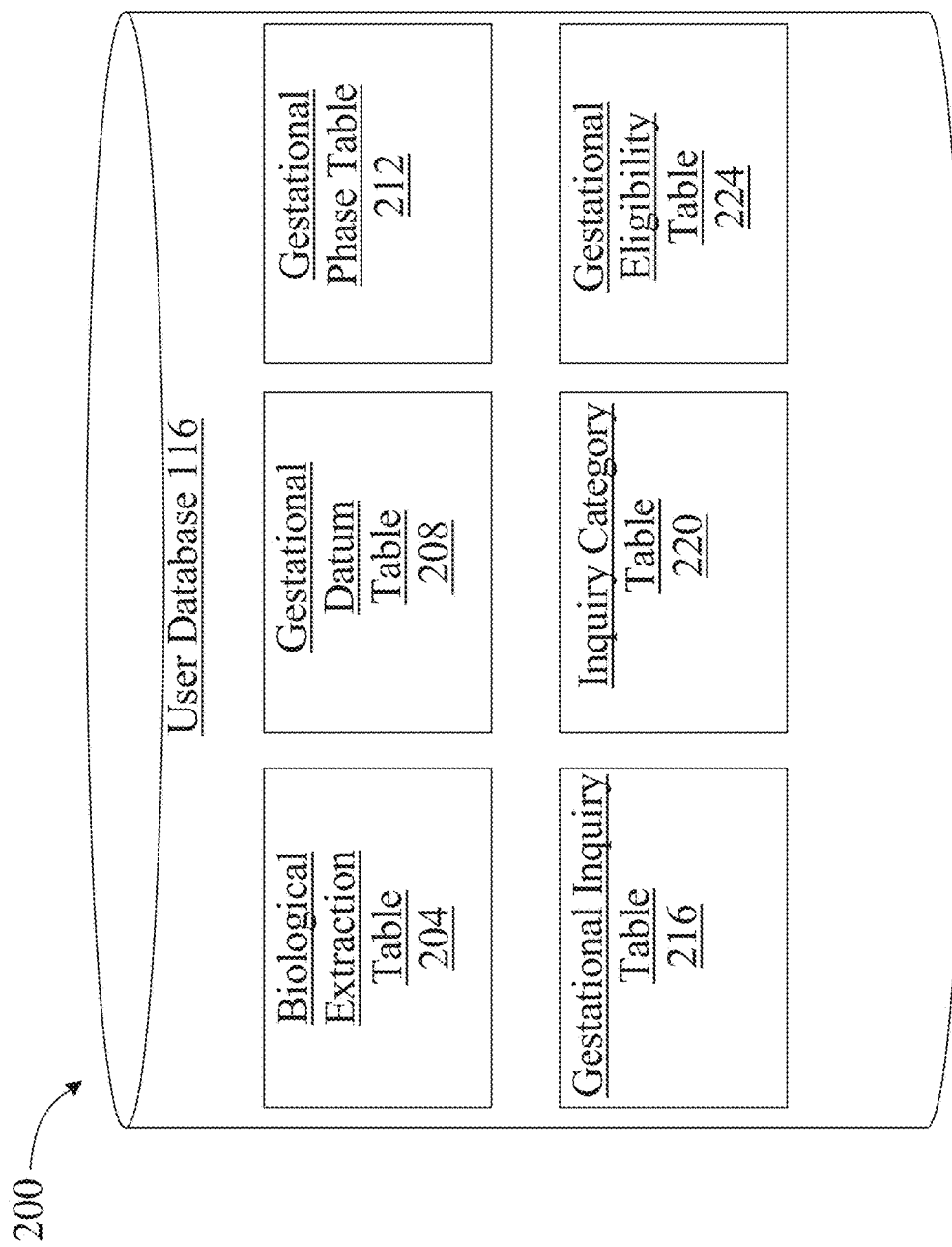
FIG. 2 is a block diagram illustrating an exemplary embodiment of a user database.

Referring now to FIG. 2, an exemplary embodiment of user database 116 is illustrated. User database 116 may be implemented as any data structure as described above in reference to FIG. 1. One or more tables contained within user database 116 may include biological extraction table 204; biological extraction table 204 may include one or more biological extraction 156 pertaining to a user. For instance and without limitation, biological extraction table 204 may include a first entry containing a stool sample analyzed for microbiome strains of bacteria and a second entry containing a blood sample taken from a microchip embedded under a user's skin to measure intracellular and extracellular levels of nutrients including vitamin B1, vitamin C, Vitamin D, Vitamin K, Vitamin E, and Vitamin A. One or more tables contained within user database 116 may include gestational datum table 208; gestational datum table 208 may include one or more gestational datum 112. For instance and without limitation, gestational datum table 208 may include a user's date of conception. One or more tables contained within user database 116 may include gestational phase table 212; gestational phase table 212 may include one or more gestational phase 108 and any corresponding dates and/or documentation. For instance and without limitation, gestational phase table 212 may indicate that a user was in the first trimester until last week when the user entered the second trimester. One or more tables contained within user database 116 may include gestational inquiry table 216; gestational inquiry table 216 may include one or more gestational inquiries generated by a user. For instance and without limitation, gestational inquiry table 216 may contain a gestational inquiry 128 that seeks to determine what type of shampoo a user can safely utilize during her pregnancy. One or more tables contained within user database 116 may include inquiry category table 220; inquiry category table 220 may include information describing one or more inquiry categories that one or more gestational inquiries have been classified to. For instance and without limitation, inquiry category table 220 may include information describing a gestational inquiry 128 pertaining to weightlifting classified to an inquiry category 140 of fitness. One or more tables contained within user database 116 may include gestational eligibility table 224; gestational eligibility table 224 may include one or more gestational eligibility labels. For instance and without limitation, gestational eligibility table 224 may include a gestational eligibility label 164 that indicates that a bamboo mattress will have a negative effect on the user.

Figure 3:
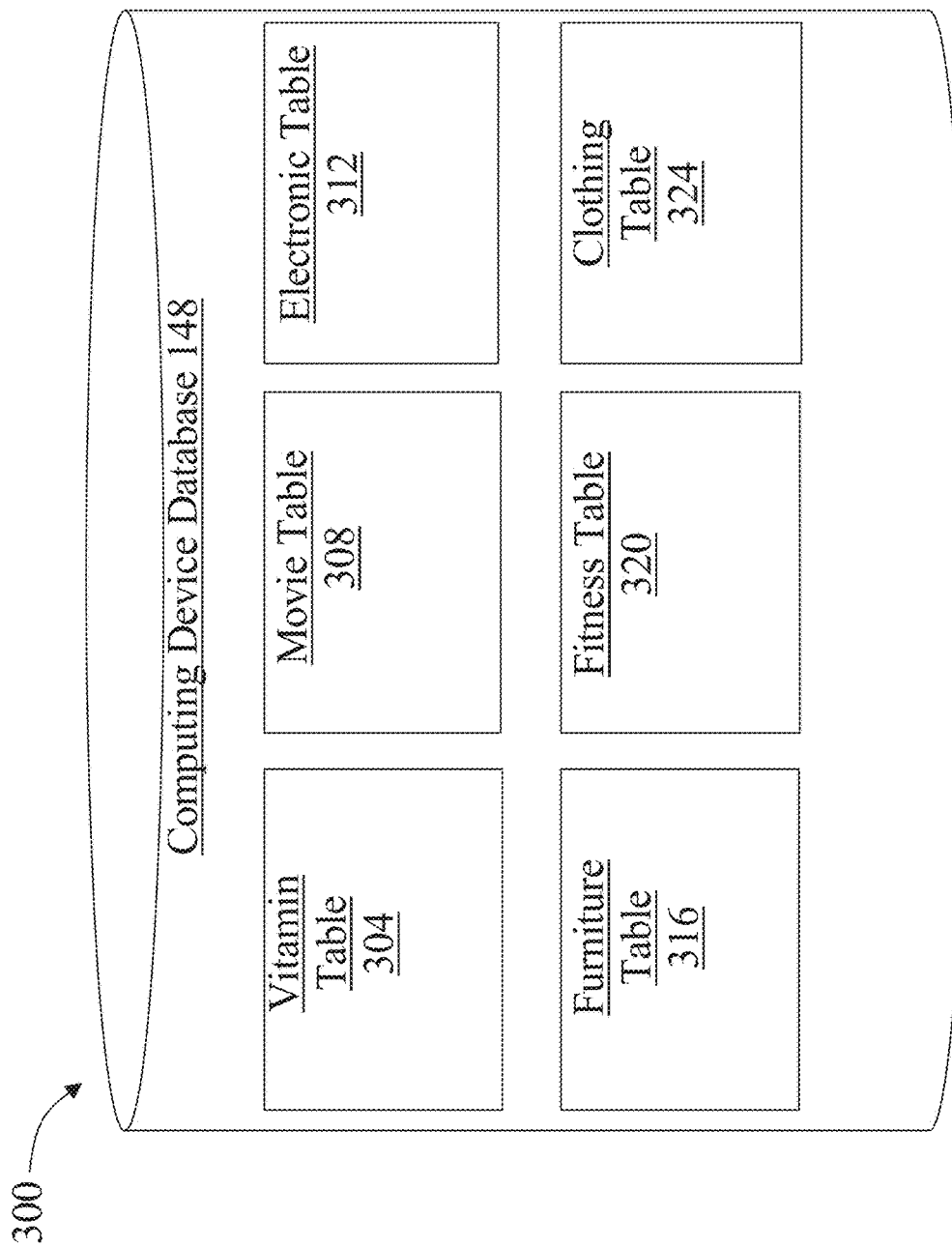
FIG. 3 is a block diagram illustrating an exemplary embodiment of a computing device database.

Referring now to FIG. 3, an exemplary embodiment of computing device database 148 is illustrated. Computing device database 148 may be implemented as any data structure as described above in reference to FIG. 1. One or more tables contained within computing device database 148 may include vitamin table 304. Vitamin table 304 may include one or more machine-learning models created for gestational inquiries classified to an inquiry category 140 of vitamin. One or more tables contained within computing device database 148 may include movie table 308; movie table 308 may include one or more machine-learning models created for gestational inquiries classified to an inquiry category 140 of movie. One or more tables contained within computing device database 148 may include electronic table 312; electronic table 312 may include one or more machine-learning models created for gestational inquiries classified to an inquiry category 140 of electronics. One or more tables contained within computing device database 148 may include furniture table 316; furniture table 316 may include one or more machine-learning models created for gestational inquiries classified to an inquiry category 140 of furniture. One or more tables contained within computing device database 148 may include fitness table 320; fitness table 320 may include one or more machine-learning models created for gestational inquiries classified to an inquiry category 140 of fitness. One or more tables contained within computing device database 148 may include clothing table 324; clothing table 324 may include one or more machine-learning models created for gestational inquiries classified to an inquiry category of clothing.

Figure 4:
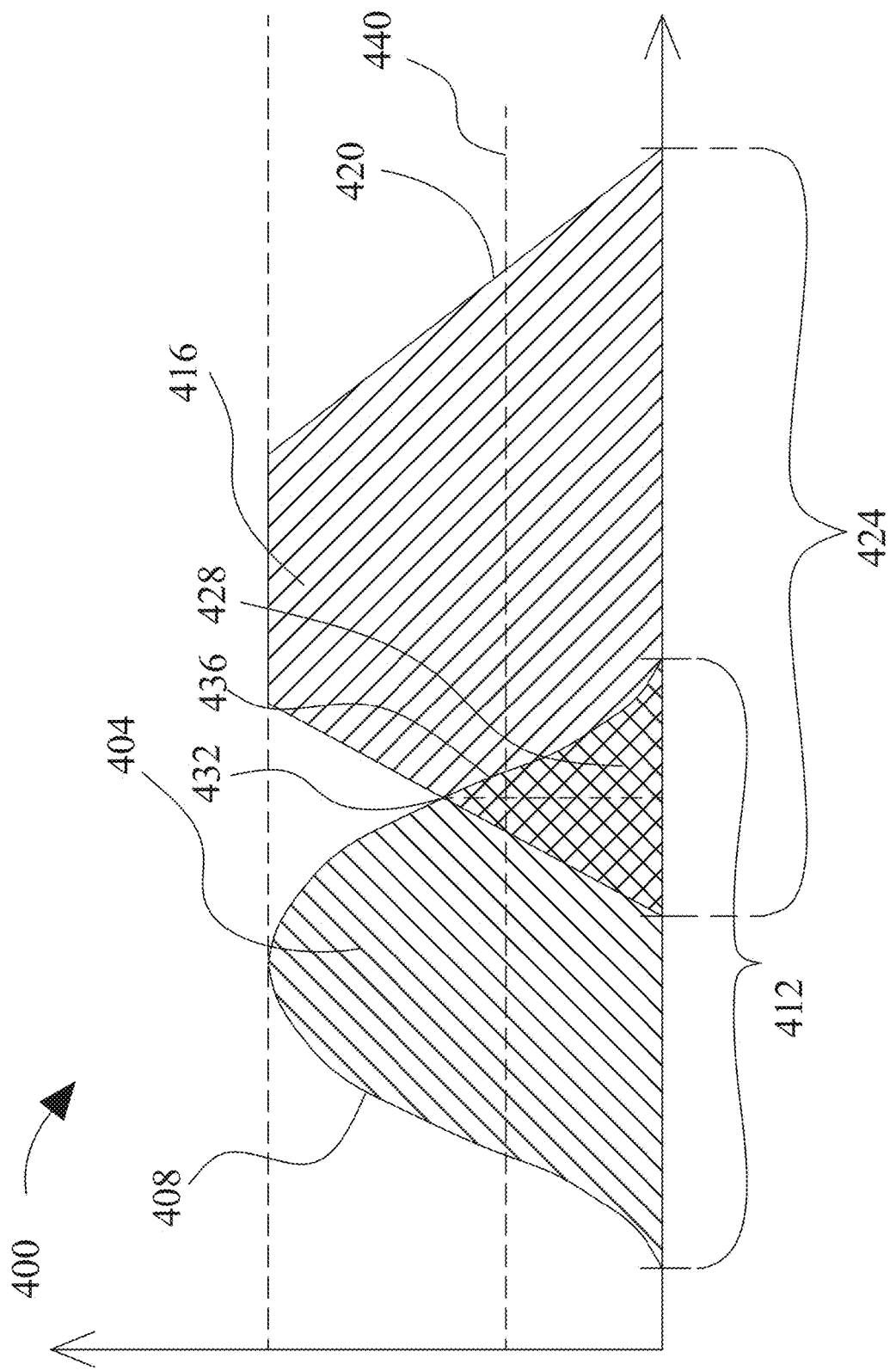
FIG. 4 is an illustration of an exemplary embodiment of fuzzy set comparison.

Now referring to FIG. 4, an exemplary embodiment of fuzzy set comparison 400 is illustrated. In a non-limiting embodiment, the fuzzy set comparison. In a non-limiting embodiment, fuzzy set comparison 400 may be consistent with fuzzy set comparison in FIG. 1. In another non-limiting the fuzzy set comparison 400 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent biological extractions 156 and gestational targets 168 from FIG. 1.

Alternatively or additionally, and still referring to FIG. 4, fuzzy set comparison 400 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 4, inference engine may be implemented according to input biological extractions 156 and examples of gestational targets 168. For instance, an acceptance variable may represent a first measurable value pertaining to the classification of biological extractions 156 to examples of gestational targets 168. Continuing the example, an output variable may represent a classification of the biological extractions 156 to examples of gestational targets 168. In an embodiment, biological extractions 156 and/or gestational targets 168 may be represented by their own fuzzy set. In other embodiments, the classification of the data into gestational targets 168 may be represented as a function of the intersection two fuzzy sets as shown in FIG. 4, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 404 may be represented, without limitation, according to a first membership function 408 representing a probability that an input falling on a first range of values 412 is a member of the first fuzzy set 404, where the first membership function 408 has values on a range of probabilities such as without limitation the interval [0,1], and an area beneath the first membership function 408 may represent a set of values within first fuzzy set 404. Although first range of values 412 is illustrated for clarity in this exemplary depiction as a range on a single number line or axis, first range of values 412 may be defined on two or more dimensions, representing, for instance, a Cartesian product between a plurality of ranges, curves, axes, spaces, dimensions, or the like. First membership function 408 may include any suitable function mapping first range 412 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 404 may represent any value or combination of values as described above, including any biological extractions 156 and examples of gestational targets 168. A second fuzzy set 416, which may represent any value which may be represented by first fuzzy set 404, may be defined by a second membership function 420 on a second range 424; second range 424 may be identical and/or overlap with first range 412 and/or may be combined with first range via Cartesian product or the like to generate a mapping permitting evaluation overlap of first fuzzy set 404 and second fuzzy set 416. Where first fuzzy set 404 and second fuzzy set 416 have a region 436 that overlaps, first membership function 408 and second membership function 420 may intersect at a point 432 representing a probability, as defined on probability interval, of a match between first fuzzy set 404 and second fuzzy set 416. Alternatively or additionally, a single value of first and/or second fuzzy set may be located at a locus 436 on first range 412 and/or second range 424, where a probability of membership may be taken by evaluation of first membership function 408 and/or second membership function 420 at that range point. A probability at 428 and/or 432 may be compared to a threshold 440 to determine whether a positive match is indicated. Threshold 440 may, in a non-limiting example, represent a degree of match between first fuzzy set 404 and second fuzzy set 416, and/or single values therein with each other or with either set, which is sufficient for purposes of the matching process; for instance, the classification into one or more query categories may indicate a sufficient degree of overlap with fuzzy set representing biological extractions 156 and examples of gestational targets 168 for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both biological extractions 156 and examples of gestational targets 168 have fuzzy sets, gestational targets 168 may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 5:
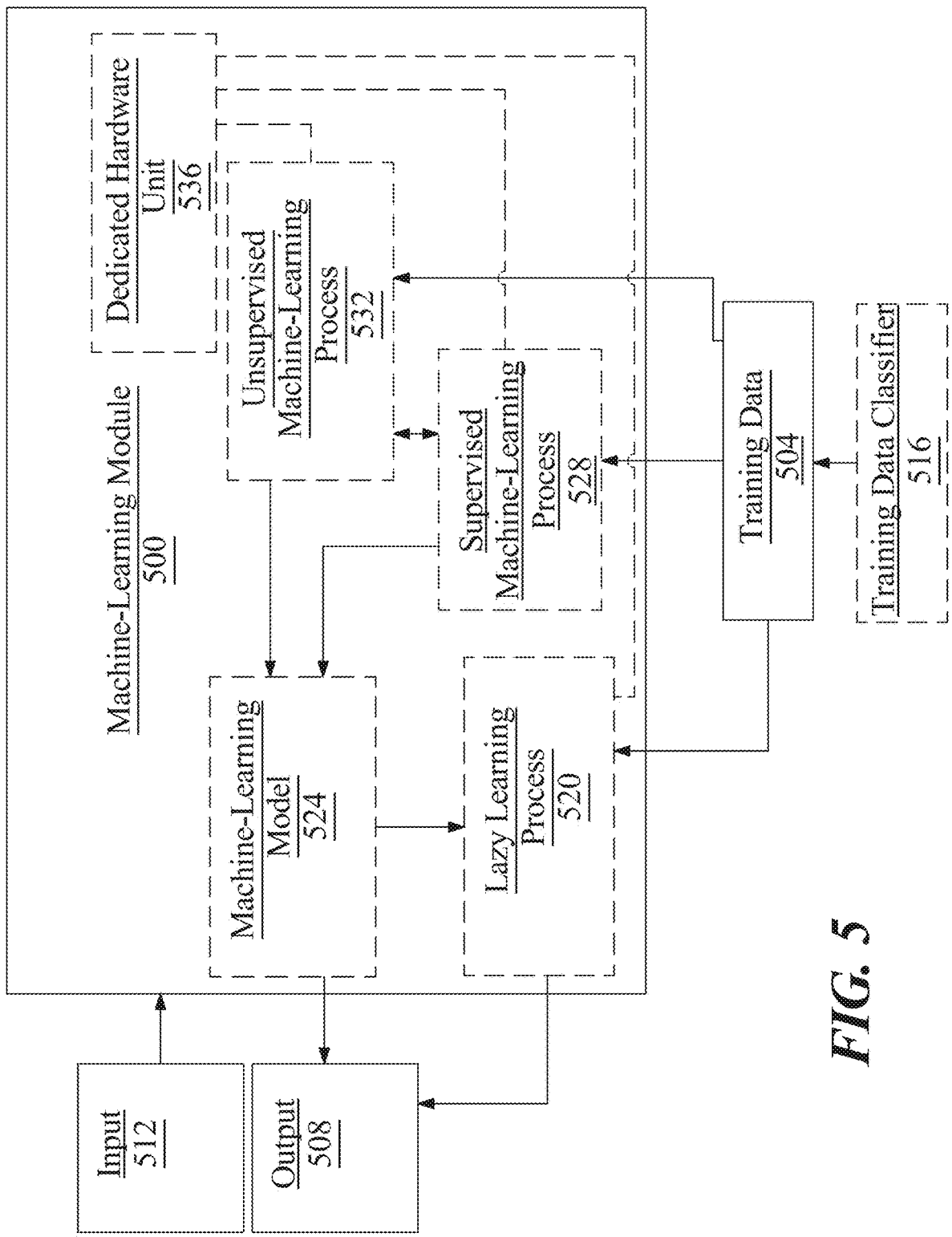
FIG. 5 is a block diagram of an exemplary machine-learning process.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example a plurality of biological extraction 156 and gestational inquiries as a inputs correlated to gestational targets 168 as outputs.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to biological extractions 156 and gestational inquires to examples of dietary suggestions.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identified as having poor quality data, where "poor quality" is defined as having a signal to noise ratio below a threshold value.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include biological extraction 156 and gestational inquires as described above as inputs, gestational targets 168 and/or gestational suggestions 172 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
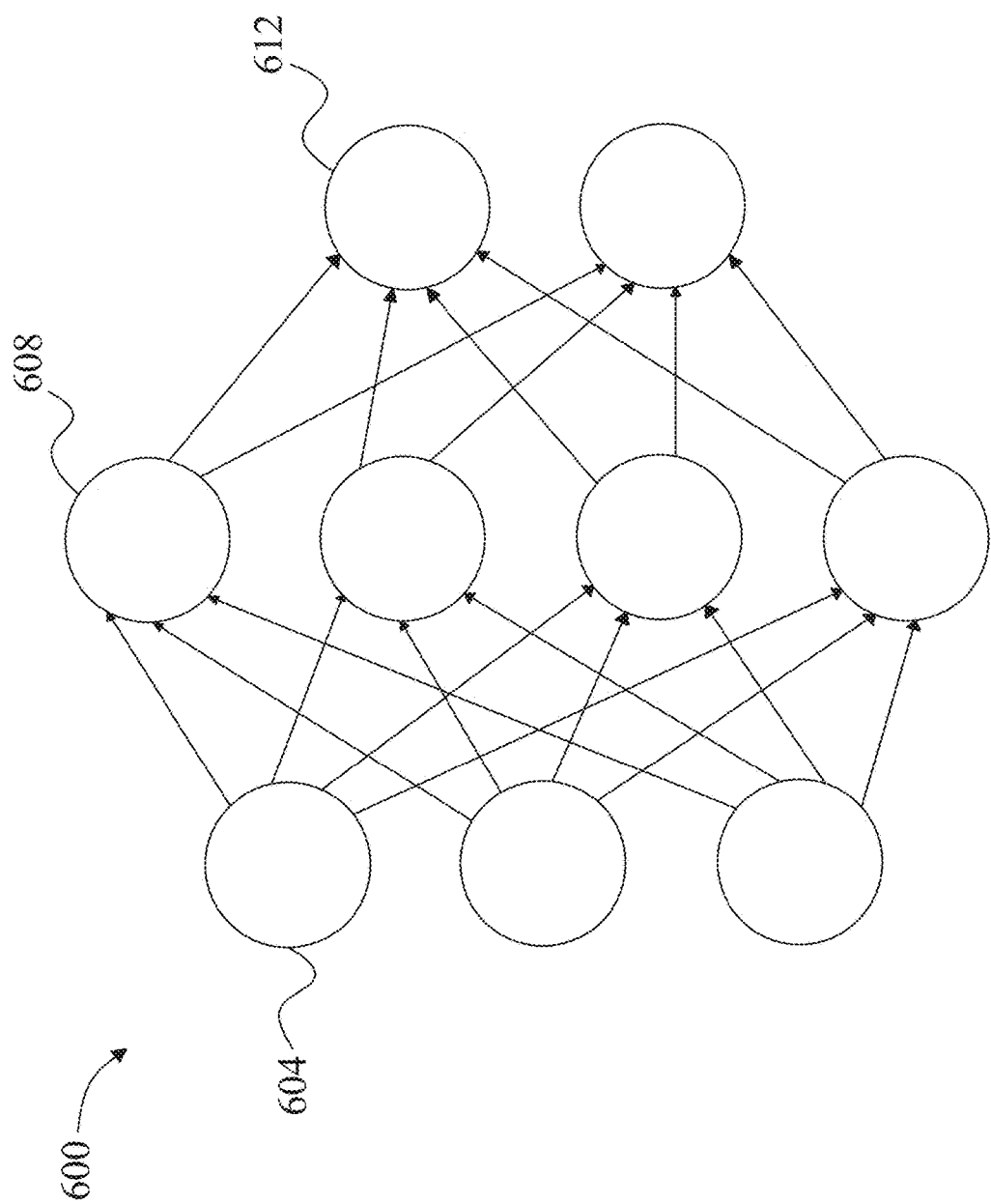
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
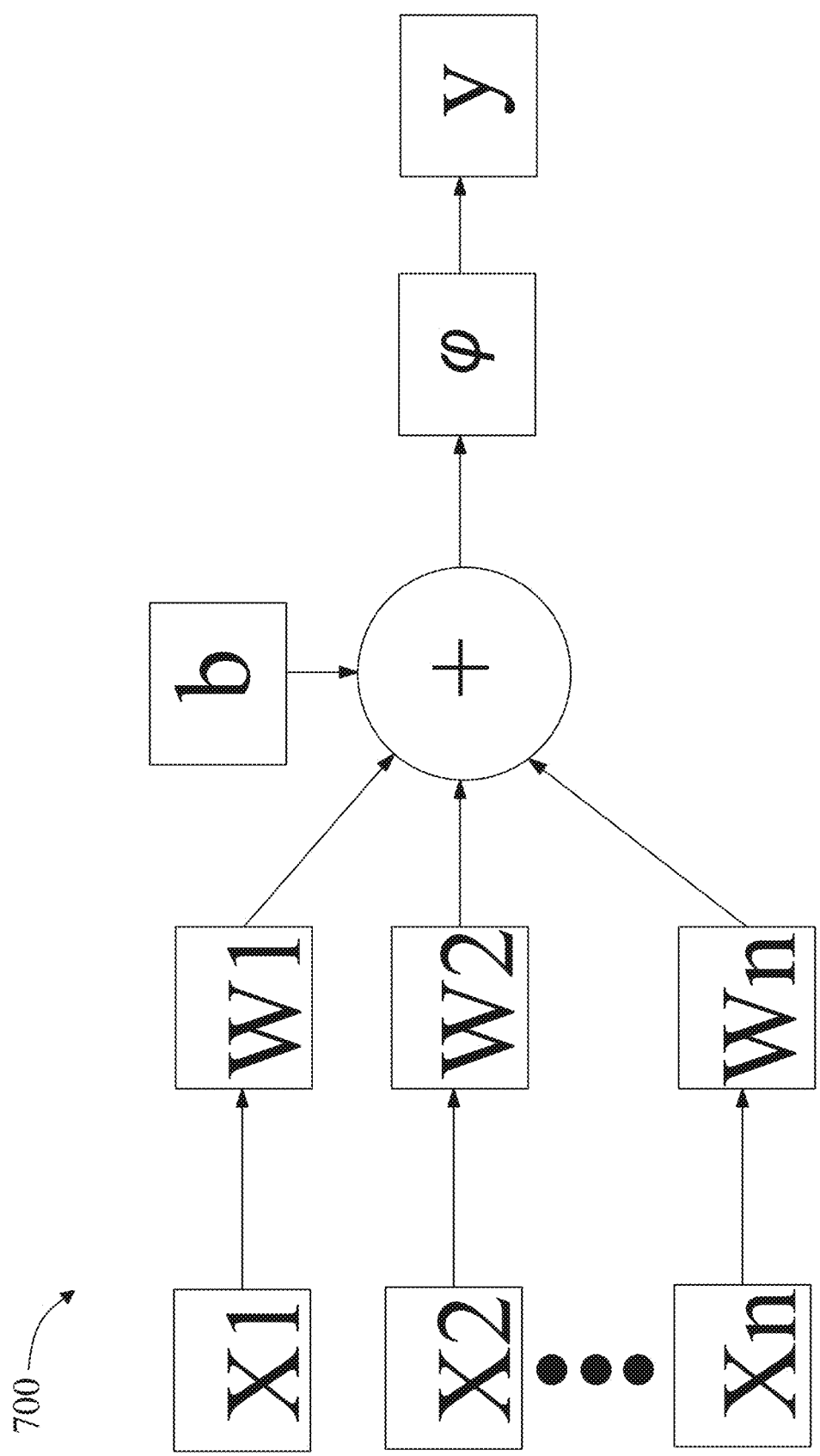
FIG. 7 is a diagram of an exemplary embodiment of a node of a neural network.

Referring now to FIG. 7, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
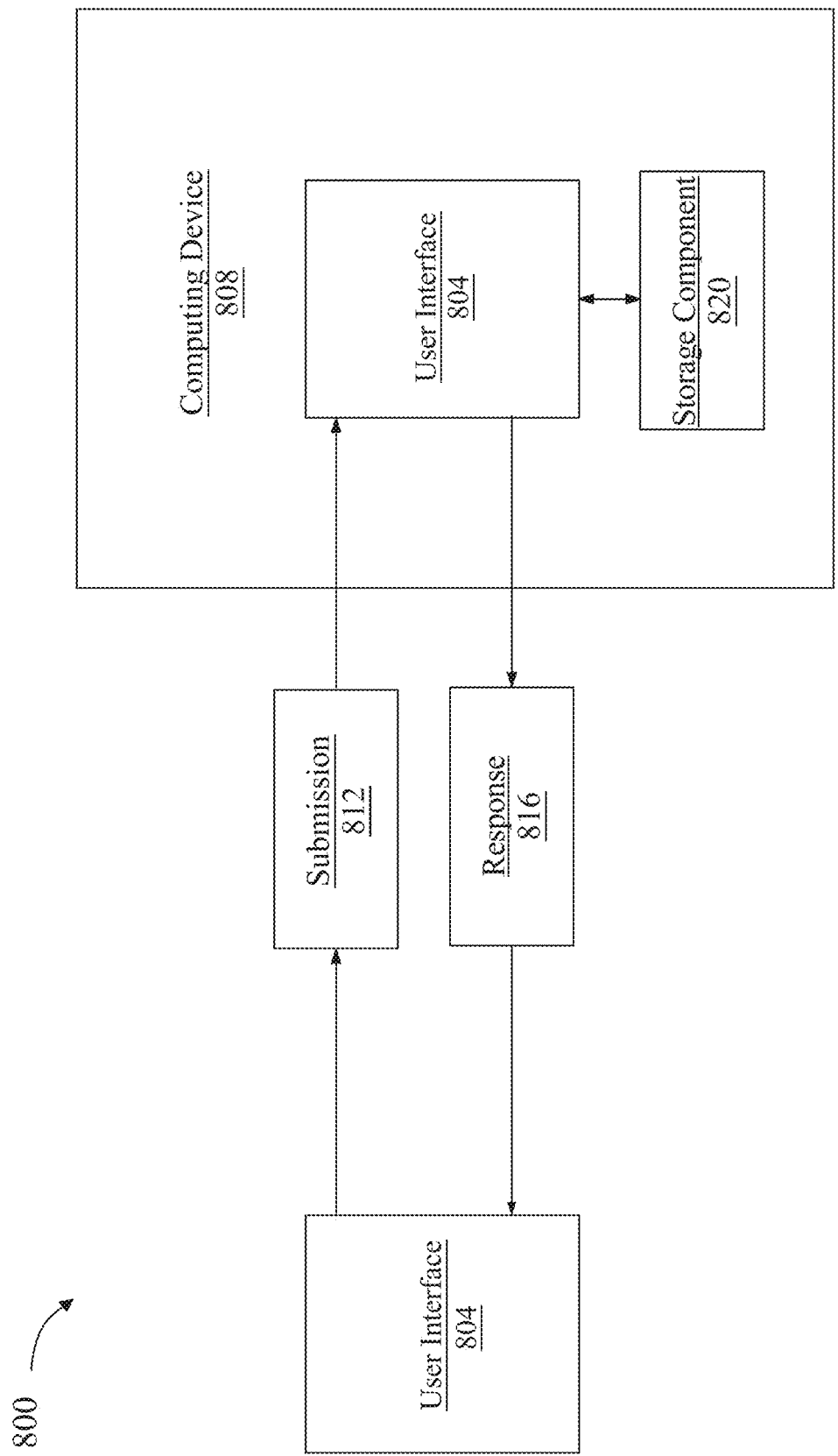
FIG. 8 is an illustration of an exemplary embodiment of a chatbot.

Referring to FIG. 8, a chatbot system 800 is schematically illustrated. According to some embodiments, a user interface 804 may be communicative with a computing device 808 that is configured to operate a chatbot. In some cases, user interface 804 may be local to computing device 808. Alternatively or additionally, in some cases, user interface 804 may remote to computing device 808 and communicative with the computing device 808, by way of one or more networks, such as without limitation the internet. Alternatively or additionally, user interface 804 may communicate with user device 808 using telephonic devices and networks, such as without limitation fax machines, short message service (SMS), or multimedia message service (MMS). Commonly, user interface 804 communicates with computing device 808 using text-based communication, for example without limitation using a character encoding protocol, such as American Standard for Information Interchange (ASCII). Typically, a user interface 804 conversationally interfaces a chatbot, by way of at least a submission 812, from the user interface 808 to the chatbot, and a response 816, from the chatbot to the user interface 804. In many cases, one or both of submission 812 and response 816 are text-based communication. Alternatively or additionally, in some cases, one or both of submission 812 and response 816 are audio-based communication.

Continuing in reference to FIG. 8, a submission 812 once received by computing device 808 operating a chatbot, may be processed by a processor. In some embodiments, processor processes a submission 812 using one or more of keyword recognition, pattern matching, and natural language processing. In some embodiments, processor employs real-time learning with evolutionary algorithms. In some cases, processor may retrieve a pre-prepared response from at least a storage component 820, based upon submission 812. Alternatively or additionally, in some embodiments, processor communicates a response 816 without first receiving a submission 812, thereby initiating conversation. In some cases, processor communicates an inquiry to user interface 804; and the processor is configured to process an answer to the inquiry in a following submission 812 from the user interface 804. In some cases, an answer to an inquiry present within a submission 812 from a user device 804 may be used by computing device 808 as an input to another function.

With continued reference to FIG. 8, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 8, computing device 808 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 808 may generate two or more decision trees, which may overlap; for instance, a root node of one tree may connect to and/or receive output from one or more terminal nodes of another tree, intermediate nodes of one tree may be shared with another tree, or the like.

Still referring to FIG. 8, computing device 808 may build decision tree by following relational identification; for example, relational indication may specify that a first rule module receives an input from at least a second rule module and generates an output to at least a third rule module, and so forth, which may indicate to computing device 808 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 808 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/ or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 8, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 9:
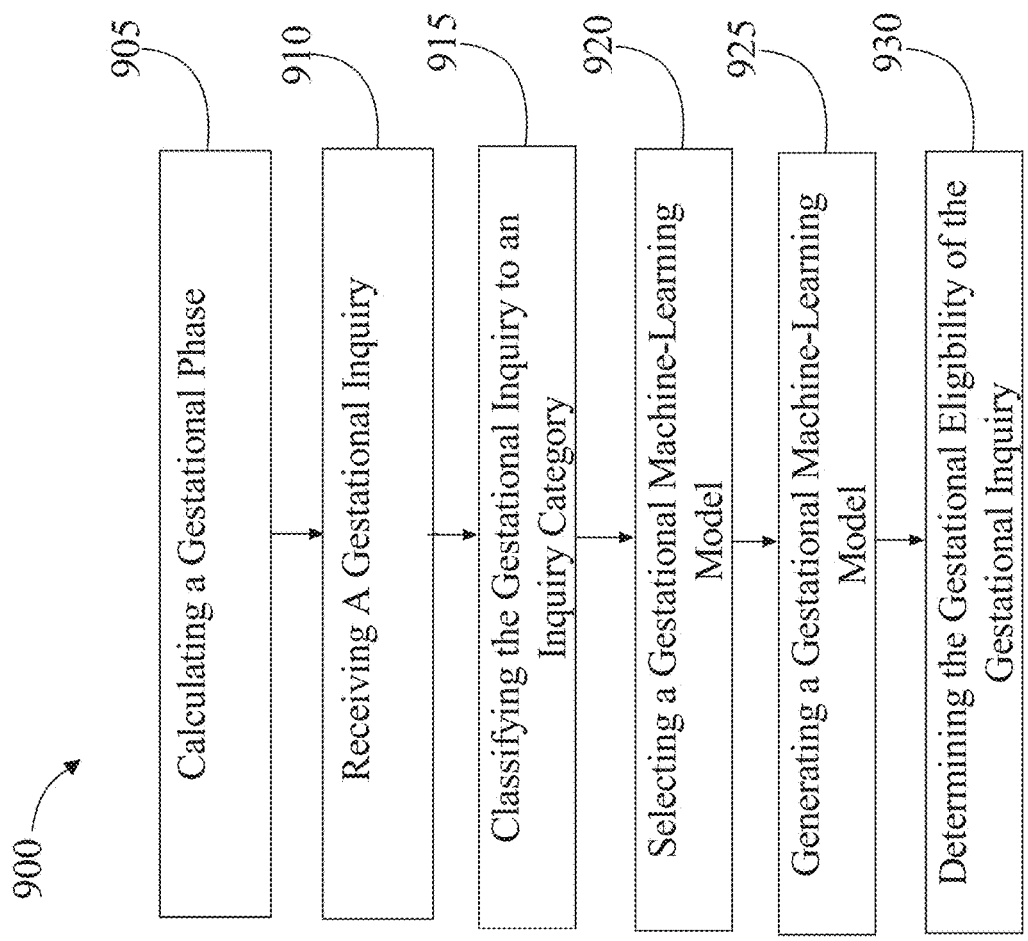
FIG. 9 is a process flow diagram illustrating an exemplary embodiment of a method of physiologically informed gestational inquiries.

With continued reference to FIG. 9, computing device 104 may calculate a gestational phase 108 utilizing a gestational datum 112. A gestational datum 112 includes any data that is utilized to calculate a gestational phase 108 as described above in more detail in reference to FIG. 1. For example, a gestational datum 112 may include a user's expected due date as calculated by a medical professional such as a user's physician. A gestational datum 112 may include an observation from an ultrasound such as how far along developed a fetus appears. One or more gestational datum 112 may be stored in user database 116 as described above in reference to FIGS. 1 and 2. Computing device 104 may receive a gestational datum 112 from a remote device 120. In an embodiment, a remote device 120 such as a mobile phone may be operated by a user who may transmit a gestational datum 112 that describes the date of the user's last menstrual period. In yet another non-limiting example, a remote device 120 such as a computer may be operated by a medical professional who may transmit a gestational datum 112 that contains an observation from a recent ultrasound. Computing device 104 may receive a gestational datum 112 from a remote device 120 utilizing any network methodology as described herein.

With continued reference to FIG. 9, computing device 104 classifies a gestational datum 112 to a gestational phase 108. Classification may be performed by generating a gestational classification algorithm 124. Gestational classification algorithm 124 includes any of the classification algorithms as described above in reference to FIG. 1. For instance and without limitation, gestational classification algorithm 124 may include logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Generating a gestational classification algorithm 124 may include generating one or more machine-learning models. Machine-learning models include any of the machine-learning models as described above in reference to FIGS. 1-8. In an embodiment, one or more machine-learning models may be stored in computing device database 148 as described above in more detail. Gestational classification algorithm 124 utilizes a gestational datum 112 as an input and outputs a gestation phase label. Gestational phase label includes any of the gestational phase labels as described above in reference to FIGS. 1-8. In an embodiment, a gestational phase label may include data that describes a user as currently being in the eighteenth week of pregnancy. In yet another non-limiting example, a gestational phase label may describe a user who is in the postpartum gestational phase and who delivered a baby three weeks prior. In an embodiment, a gestational phase label may indicate and describe how many fetuses are developing inside a user and/or how many babies were delivered. For instance and without limitation, a gestational phase label may indicate that a user is currently pregnant with twins and is currently in her second trimester of pregnancy. In yet another non-limiting example, a gestational phase label may indicate that a user is in the postpartum phase having delivered triplets the previous day. In an embodiment, a gestational phase label may indicate the sex of a fetus and/or the sex of a delivered baby. For instance and without limitation, a gestational phase label may indicate that a user is in the thirty fourth week of the third trimester and is currently pregnant with a female fetus. Computing device 104 generates a gestational phase label containing a description of the gestational phase 108 and any other information described herein utilizing any methodology as described herein.

With continued reference to FIG. 9, at step 910, computing device 104 receives from a remote device 120 operated by a user a gestational inquiry 128. A gestational inquiry, as used in this disclosure, contains a description of any advice sought and/or question relating to any area of a user's life. For instance and without limitation, a gestational inquiry 128 may seek to know what body lotion will be compatible for the user's body while also being safe for the fetus. In yet another non-limiting example, a gestational inquiry 128 may seek to know what seafood is safe to consume while the user is actively trying to become pregnant. In yet another non-limiting example, a gestational inquiry 128 may seek to understand what vaccinations are safe to receive during pregnancy. In yet another non-limiting example, a gestational inquiry may seek to discover what over the counter medication the user should take for an upset stomach while the user is nursing her daughter. In yet another non-limiting example, a gestational inquiry 128 make seek to know what medical procedure the user should have performed while three weeks pregnant for a slipped disc. In yet another non-limiting example, a gestational inquiry 128 may seek to question what type of paint the user should paint user's bedroom while the user is seeking to become pregnant. In yet another non-limiting example, a gestational inquiry 128 may seek to know what recreational activities the user can engage in such as skiing, weightlifting, and/or water sports. In yet another non-limiting example, a gestational inquiry 128 may seek to know what cleaning products the user can use to clean the user's house. In yet another non-limiting example, a gestational inquiry 128 may seek to discover how much caffeine a user can consume and tolerate while pregnant if at all. In yet another non-limiting example, a gestational inquiry 128 may seek to know what types of exercise a user can engage while the user is actively trying to become pregnant. In yet another non-limiting example, a gestational inquiry 128 may seek to understand what prescription medication a user can take while six months pregnant when the user experiences a migraine headache.

With continued reference to FIG. 9, computing device 104 may receive an image of a gestational inquiry 128. Computing device 104 may contain an image catching device 132 that may receive a wireless transmission from a remote device 120 that contains a picture of a gestational inquiry 128. For instance and without limitation, a user may take a picture or photograph of a pillow that a user purchased to determine if the pillow is safe for the user to sleep on each night. In yet another non-limiting example, a user may take a picture of a uniform code commission barcode located on an electronic device to determine the compatibility of the electronic device for the user. In an embodiment, image catching device 132 may be located on remote device 120. For example, a remote device 120 such as a mobile phone may contain a camera or scanner that may allow a user to obtain a picture and/or photograph of a gestational inquiry 128. In an embodiment, a user may browse an online marketplace and may transmit to an image catching device 132 located on computing device 104 a photograph of a product available for sale online such as a kitchen utensil composed of plastic.

With continued reference to FIG. 9, computing device 104 may receive a gestational inquiry 128 that contains a description of a gestational inquiry. A description may contain a textual narrative describing a gestational inquiry 128. For instance and without limitation, a description may contain a textual narrative that describes a series of symptoms that a user has been experiencing, including a burning feeling in the chest behind the breastbone that occurs after eating and that lasts for several hours, chest pain after bending over, burning in the throat, and a hot sour tasting fluid at the back of the throat. In such an instance, the description may also contain a question asking what over the counter medication the user can consume that will alleviate the user's symptoms. Computing device 104 separates a gestational inquiry 128 from a description of a gestational inquiry. In the above referenced example, computing device 104 may separate the description to generate a gestational inquiry 128 that indicates a question regarding an over the counter medication that can alleviate symptoms of burning and chest pain. Computing device 104 may separate a description to generate a gestational inquiry 128 utilizing language processing module 136. This may be performed utilizing any of the methodologies as described above in reference to FIG. 1. In yet another non-limiting example, computing device 104 may receive a gestational inquiry 128 that contains a description that includes details containing a description of twenty five different brands of shampoo with a question that indicates a willingness to know what brand of shampoo is best suited for the user who is seven weeks pregnant. In such an instance, computing device 104 may separate the description regarding the twenty five different brands of shampoo to create a gestational inquiry 128 that contains a desire to know what shampoo is most compatible for a user who is seven weeks pregnant.

With continued reference to FIG. 9, at step 915, computing device 104 classifies a gestational inquiry 128 to an inquiry category 140. Classification may be performed utilizing any of the classification algorithms as described above in reference to FIG. 1. Classification may include generating a category classification algorithm 144. Category classification algorithm 144 includes any of the classification algorithms as described above in reference to FIG. 1. In an embodiment, category classification algorithm 144 utilizes a gestational inquiry 128 as an input and outputs an inquiry category 140. Inquiry category 140 includes any data that categorizes a gestational inquiry 128 as having relevance to a particular topic as described above in reference to FIG. 1. Inquiry category 140 may indicate what aspect or area of a user's life that a gestational inquiry relates to. For instance and without limitation, an inquiry category 140 may indicate that a gestational inquiry that contains advice about the best mascara to utilize may relate to an inquiry category 140 of cosmetics. In yet another non-limiting example, an inquiry category 140 may indicate that a gestational inquiry 128 that contains a question about what types of meats to consume while pregnant may relate to an inquiry category 140 of nutrition. In an embodiment, an inquiry category 140 may contain one or more sub-categories that contain a further delineation of an inquiry category 140 into subsequent, more refined inquiry categories. For instance and without limitation, a gestational inquiry 128 may contain advice about what fabric sweater the user should wear. In such an instance, computing device 104 may classify the previously described gestational inquiry 128 to an inquiry category 140 of clothing and further assign it to a sub-category that includes women's tops.

With continued reference to FIG. 9, at step 920, computing device 104 selects a gestational machine-learning model 152 as a function of an inquiry category 140. Gestational machine-learning model 152 includes any of the machine-learning models as described above in reference to FIG. 1. In an embodiment, computing device 104 may select one or more gestational machine-learning model 152 from computing device database 148. In an embodiment, computing device 104 may match an inquiry category 140 to a machine-learning model intended for the inquiry category 140. This may be performed utilizing language processing module 136. For instance and without limitation, an inquiry category 140 may be generated for electronics which computing device 104 may match to a machine-learning model intended for electronics stored within computing device database 148. In an embodiment, one or more machine-learning models may be organized within computing device database 148 based on the inquiry category 140 that the machine-learning model relates to. For instance and without limitation, an inquiry category 140 may be generated for indoor house plants, which computing device 104 may match to a machine-learning model intended for indoor house plants.

With continued reference to FIG. 9, at step 925, computing device 104 generates a gestational machine-learning model 152. Gestational machine-learning model 152 utilizes a gestational phase label and a user biological extraction 156 as an input and outputs gestational eligibility. Gestational eligibility includes an indication of either a positive or negative effect on a user's body based on the user's gestational phase 108 and the user's constitution as indicated by the user's biological extraction 156. Gestational eligibility may indicate if a particular product or activity included in a gestational inquiry 128 is compatible with a user's biological extraction 156 and a user's gestational phase 108. For instance and without limitation, gestational eligibility may indicate that a deep hair condition that contains methylparaben is compatible for the user's biological extraction 156 which shows the user does not have a methylenetetrahydrofolate reductase mutation (MTHFR) indicating that the user is able to excrete methylparaben and not store methylparaben within the user's body. In such an instance, gestational eligibility may indicate that while the methylparaben is compatible with the user's biological extraction 156, methylparaben is not compatible with the user's gestational phase 108 because the user is in the first trimester and methylparaben may cause birth defects within the first trimester. In such an instance, gestational eligibility may indicate that overall, methylparaben will have a negative effect on the user's body. In yet another non-limiting example, gestational eligibility may indicate that an activity such as riding in a hot air balloon will have a positive effect on a user's body because riding in a hot air balloon is compatible with the user's biological extraction 156, and is safe to engage in when based on the user's current gestational phase 108.

With continued reference to FIG. 9, computing device 104 may generate gestational machine-learning model 152 utilizing gestational training data 160. Gestational training data 160 includes any of the training data as described above in reference to FIG. 1. Gestational training data 160 includes a plurality of gestational phase labels and biological extraction 156 correlated to gestational eligibility. In an embodiment, gestational training data 160 may be stored within computing device database 148. Computing device 104 may output utilizing gestational machine-learning model a plurality of gestational eligibility labels for gestational inquiries related to an inquiry category 140. Gestational eligibility label includes any data that describes gestational eligibility. In an embodiment, computing device 104 may generate a plurality of gestational eligibility labels related to an inquiry category 140. For instance and without limitation, computing device 104 may generate a plurality of gestational eligibility label 164 related to twenty five different types of shampoo for a gestational inquiry 128 related to shampoo and classified to an inquiry category 140 of cosmetics. In yet another non-limiting example, computing device 104 may generate a plurality gestational eligibility label 164 related to all different types of exercise for a gestational inquiry related to exercise and classified to an inquiry category 140 of fitness.

With continued reference to FIG. 9, at step 930, computing device 104 determines utilizing a gestational machine-learning model 152 the gestational eligibility of a gestational inquiry. In an embodiment, determining the gestational eligibility of a gestational inquiry 128 may include evaluating the positive and/or negative effect of a gestational inquiry 128 on a user's biological extraction 156 and the user's gestational phase 108. Computing device 104 may determine that a gestational inquiry 128 is suitable for a user based on the user's current gestational phase 108. In such an instance, computing device 104 evaluates a gestational inquiry 128 to determine eligibility for subsequent gestational phase 108. For instance and without limitation, computing device 104 may determine that a gestational inquiry 128 for an activity such as skiing is suitable for a user in the preconception phase, conception, and implantation phase, and the first trimester phase, but not in the second trimester phase, third trimester phase, and the postpartum phase. In yet another non-limiting example, computing device 104 may determine that a gestational inquiry for a particular brand protein bar may be suitable for all gestational phase 108 include preconception, conception, and implantation, first trimester, second trimester, third trimester, a postpartum phase. Computing device 104 may determine that a gestational inquiry 128 is suitable for a user and initiate a limitation on a gestational inquiry. A limitation may include any restriction placed on a gestational inquiry 128 as described above in reference to FIG. 1. For instance and without limitation, a limitation may specify that a user can take a cough medicine during the third trimester, but the user cannot use more than two doses per day. In yet another non-limiting example, a limitation may specify that a user can participate in a spinning class at a gym, but the user cannot have a heart rate above 120 beats per minute, otherwise the user must slow down. In yet another non-limiting example, a limitation may specify that a user can use a certain deodorant as much as the user wants during the preconception phase and conception and implantation phase, but the user can only use the deodorant no more than three times each week during the first trimester phase, the second trimester phase, the third trimester phase, and the user cannot use the deodorant at all during the postpartum phase.

With continued reference to FIG. 9, computing device 104 may determine that a gestational inquiry is not suitable for a user and as such may identify suitable gestational inquiries related to an inquiry category 140. For instance and without limitation, computing device 104 may determine that a snake plant is not suitable for a user, where a snake plant may relate to a gestational inquiry 128 classified to an inquiry category 140 of indoor houseplants. In such an instance, computing device 104 identify suitable indoor houseplants which may include for example, bromeliads, jade, pothos, rabbit's ear, and rubber plant. In such an instance, computing device 104 may recommend suitable gestational inquiries related to an inquiry category 140 based on a user's biological extraction 156 and a user gestational phase 108. In the above described example, computing device 104 may identify suitable indoor houseplants by ensuring that the identified suitable indoor houseplants are suitable for the user's biological extraction 156 and the user's gestational phase 108. Computing device 104 may determine that a gestational inquiry 128 is not suitable for a first gestational phase 108 but the gestational inquiry 128 is suitable for a second gestational phase 108 where the second gestational phase 108 occurs after the first gestational phase 108. For instance and without limitation, computing device 104 may determine that hair dye is not suitable in the conception and implantation phase and the first trimester phase, but hair dye is suitable in the second trimester phase, the third trimester phase, and the postpartum phase. In yet another non-limiting example, computing device 104 may determine that mahi mahi is not suitable in the first trimester phase and the second trimester phase but mahi mahi is suitable in the third trimester phase and in the postpartum phase.

Figure 10:
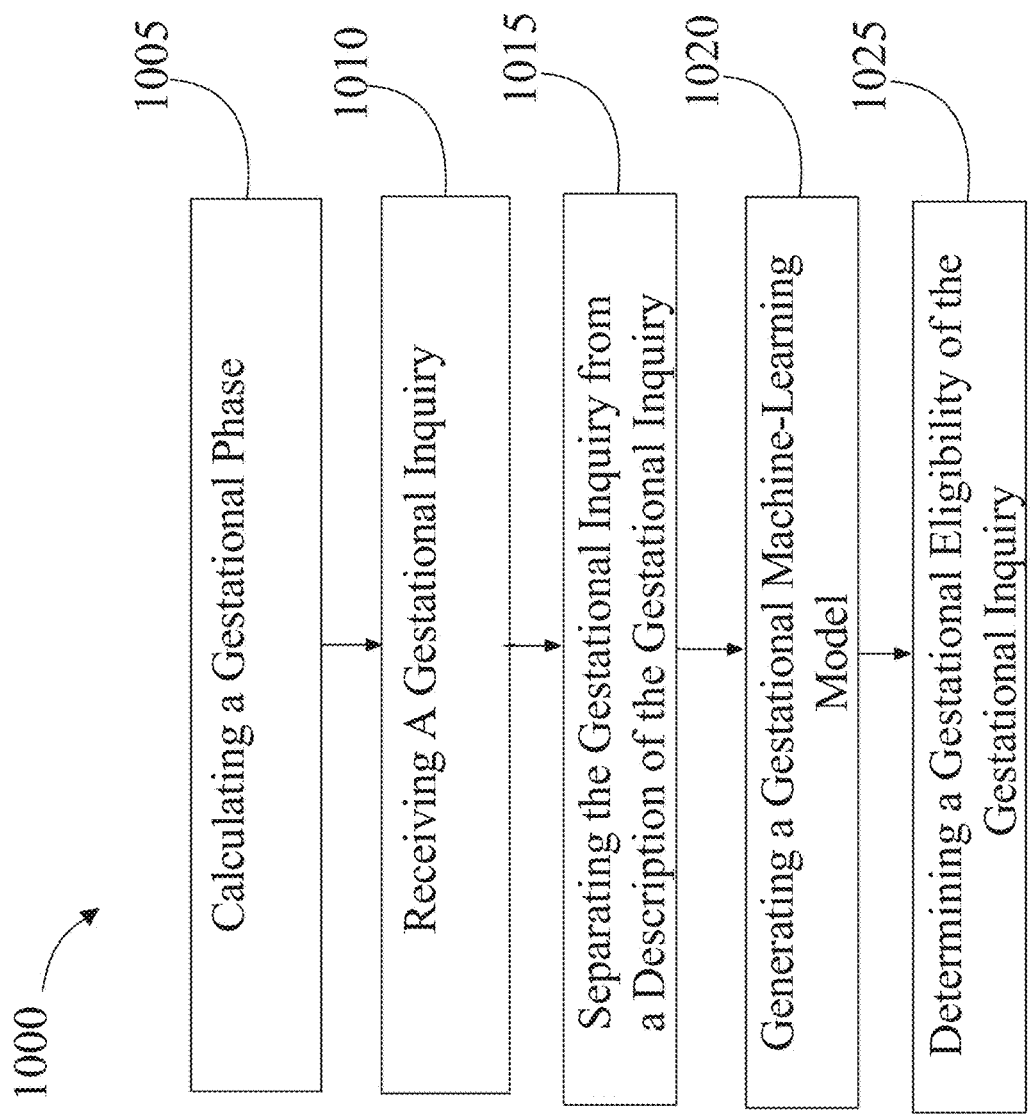
FIG. 10 is a process flow diagram illustrating an exemplary embodiment of a method of physiologically informed gestational inquiries.

Referring now to FIG. 10, an exemplary embodiment of a method 1000 of physiologically informed gestational inquiries is illustrated. At step 1005, method 1000 includes calculating by a computing device, a gestational phase, for example and with reference to FIGS. 1-9. Calculating the gestational phase may include receiving a gestational datum; classifying the gestational datum to a gestational phase; and generating a gestational phase label as a function of the classifying. In an embodiment, classifying the gestational datum to a gestational phase may include generating a gestational classification algorithm, wherein the gestational classification algorithm utilizes the gestational datum as an input and outputs a gestational phase label. At step 1010, method 500 includes, receiving by the computing device, from a remote device operated by a user, a gestational inquiry, for example and with reference to FIGS. 1-10. Receiving the gestational inquiry may include receiving by the computing device, at an image catching device located on the computing device, a wireless transmission from the remote device containing a picture of the gestational inquiry. In an embodiment, step 1010 may also include classifying the gestational inquiry to an inquiry category; and selecting by the computing device, a gestational machine-learning model as a function of the inquiry category.

Still referring to FIG. 10, at step 1015, method 1000 includes separating, by the computing device, a gestational inquiry from a description of the gestational inquiry, for example, and with reference to FIGS. 1-10. Separating the gestational inquiry from the description of the gestational inquiry may include utilizing a language processing module. At step 1020, method 1000 includes generating by the computing device, a gestational machine-learning model, wherein the gestational machine-learning model utilizes the gestational phase label and a user biological extraction as an input and outputs gestational eligibility labels, for example and with reference to FIGS. 1-10. The biological extraction may include at least an element of physiological data, wherein the at least an element of physiological data includes hematological data. At step 1025, method 1000 includes determining by the computing device, utilizing the gestational machine-learning model, the gestational eligibility of the gestational inquiry, for example and with reference to FIGS. 1-10. Determining the gestational eligibility of the gestational inquiry may include evaluating at least a positive effect of the gestational inquiry on the user's biological extraction and gestational phase.

Figure 11:
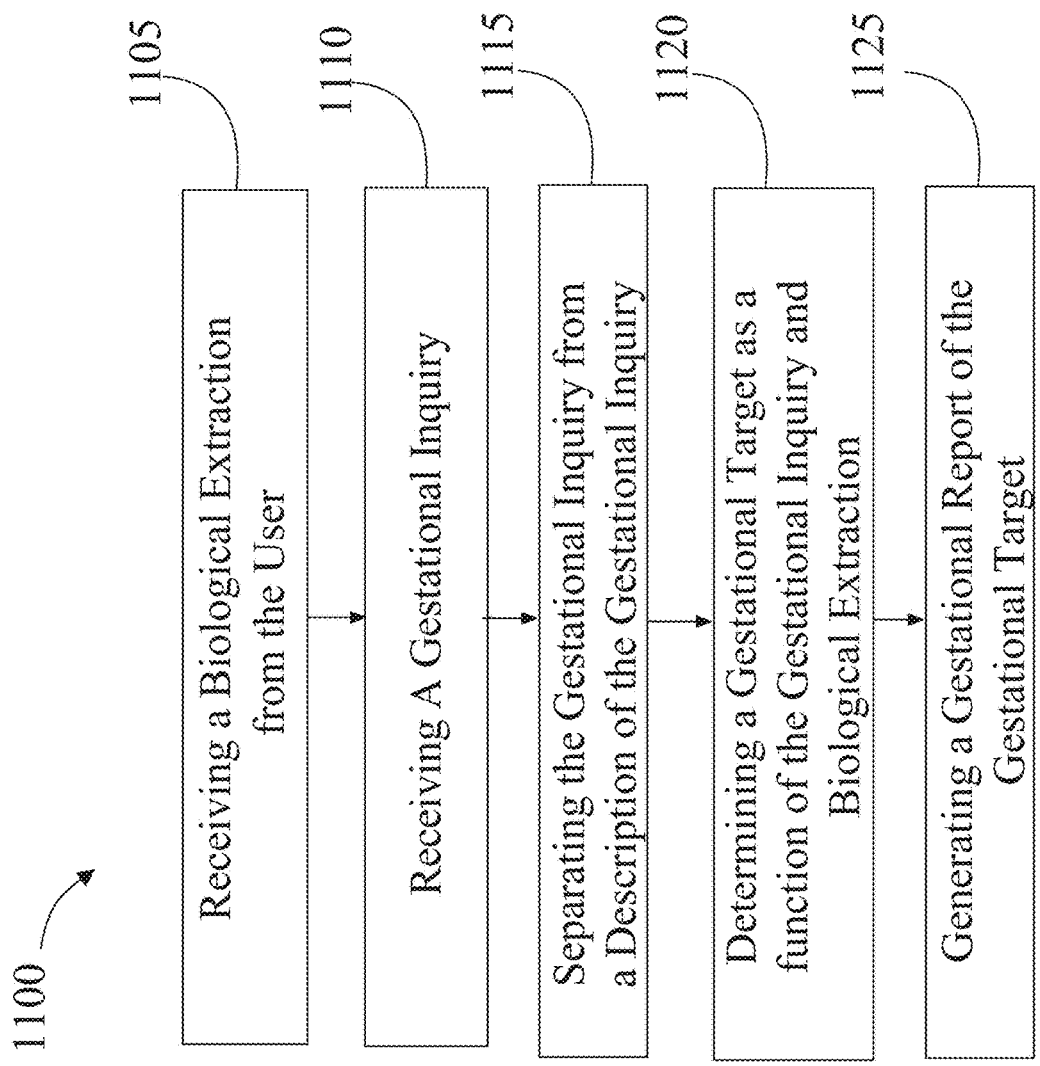
FIG. 11 is a process flow diagram illustrating an exemplary embodiment of a method of physiologically informed gestational inquiries.

Referring now to FIG. 11, a flow diagram of an exemplary method 1100 for physiologically informed gestational inquiries is illustrated. At step 1105, method 1100 includes receiving, using at least a processor, a biological extraction from the user. This may be implemented as described and with reference to FIGS. 1-10. In an embodiment, the biological extraction may further include at least an element of physiological data.

Still referring to FIG. 11, at step 1110, method 1100 includes receiving, using the at least a processor, a gestational inquiry from the user. This may be implemented as described and with reference to FIGS. 1-10.

Still referring to FIG. 11, at step 1115, method 1100 includes separating, using the at least a processor, the gestational inquiry from a description of the gestational inquiry. This may be implemented as described and with reference to FIGS. 1-10.

Still referring to FIG. 11 at step 1120, method 1100 includes determining, using the at least a processor, a gestational target as a function of the gestational inquiry and the biological extraction. This may be implemented as described and with reference to FIGS. 1-10. In an embodiment, determining the gestational target may include determining a nutritional threshold for the user. In another embodiment, determining the gestational target may include identifying one or more gestational suggestions as a function of the gestational inquiry and the biological extraction. In some cases, the gestational suggestion may include a dietary suggestion and/or a fitness suggestion. In an embodiment, the method may further include determining, using the at least a processor, a gestational eligibility of the gestational target. In some cases, determining the gestational eligibility of the gestational target may further include evaluating at least a positive effect of the gestational target on the user's biological extraction and gestational phase.

Still referring to FIG. 11 at step 1125, method 1100 includes generating, using the at least a processor, a gestational report as a function of the gestational target. This may be implemented as described and with reference to FIGS. 1-10. In an embodiment, generating the gestational report may include generating the gestational report using a large language model. In some cases, determining the gestational target further may additionally include specifically training the target machine-learning model using training data, wherein the training data comprises a plurality of biological extractions from users within the same gestational phase as the current user as inputs correlated to gestational targets as a outputs.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
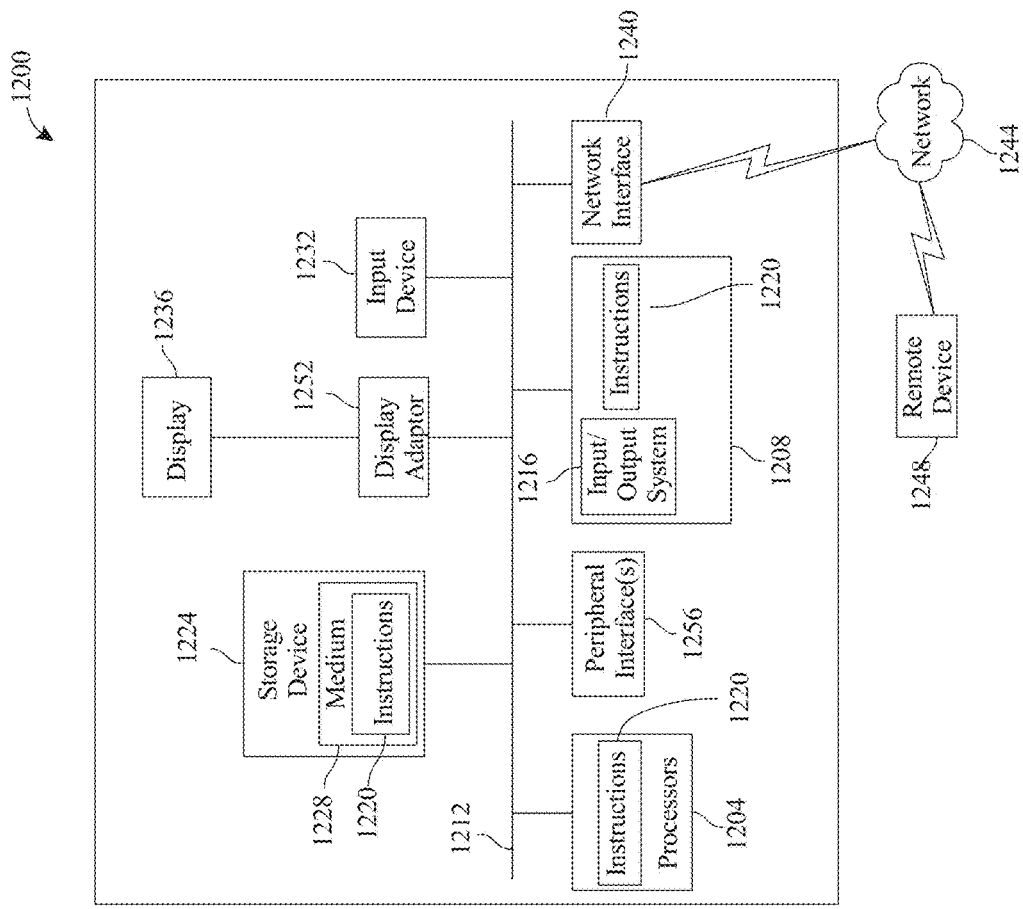
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Processor 1204 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1204 may be organized according to Von Neumann and/or Harvard architecture as a non-limiting example. Processor 1204 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1208 may include various components (e.g., machine-readable media) including, but not limited to, a random-access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display device 1236. Examples of a display device include, but are not limited to, a liquid crystal display (LCD), a cathode ray tube (CRT), a plasma display, a light emitting diode (LED) display, and any combinations thereof. Display adapter 1252 and display device 1236 may be utilized in combination with processor 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for physiologically informed gestational inquiries,
    wherein the apparatus comprises:
    at least a processor;
    a memory communicatively connected to the at least a processor, the memory containing instructions configuring the at least a processor to:
        receive a biological extraction from a user;
        receive a gestational inquiry from the user;
        separate the gestational inquiry from a description of the gestational inquiry;
        determine a gestational target as a function of the gestational inquiry and the biological extraction, wherein determining the gestational target further comprises:
            iteratively training a target machine-learning model using target training data, wherein target training data comprises a plurality of gestational inquiries as inputs correlated to examples of gestational targets as outputs; and
            determining the gestational target as a function of the gestational inquiry using a trained target machine-learning model; and
        generate a gestational report as a function of the gestational target.

2. The apparatus of claim 1, wherein determining the gestational target comprises determining a nutritional threshold for the user.

3. The apparatus of claim 1, wherein generating the gestational report comprises generating the gestational report using a large language model.

4. The apparatus of claim 1, wherein determining the gestational target further comprises specifically training the target machine-learning model using training data, wherein the training data comprises a plurality of biological extractions from users within a same gestational phase as the user as inputs correlated to gestational targets as outputs.

5. The apparatus of claim 1, wherein determining the gestational target comprises identifying one or more gestational suggestions as a function of the gestational inquiry and the biological extraction.

6. The apparatus of claim 5, wherein the one or more gestational suggestions comprises a dietary suggestion.

7. The apparatus of claim 5, wherein the one or more gestational suggestions comprises a fitness suggestion.

8. The apparatus of claim 1, wherein the biological extraction further comprises at least an element of physiological data.

9. The apparatus of claim 1, the memory further instructs the processor to determine a gestational eligibility of the gestational target.

10. The apparatus of claim 9, wherein determining the gestational eligibility of the gestational target further comprises evaluating at least a positive effect of the gestational target on the user's biological extraction and gestational phase.

11. A method for physiologically informed gestational inquiries,
wherein the method comprises:
receiving, using at least a processor, a biological extraction from a user;
receiving, using the at least a processor, a gestational inquiry from the user;
separating, using the at least a processor, the gestational inquiry from a description of the gestational inquiry;
determining, using the at least a processor, a gestational target as a function of the gestational inquiry and the biological extraction, wherein determining the gestational target further comprises:
iteratively training a target machine-learning model using target training data, wherein target training data comprises a plurality of gestational inquiries as inputs correlated to examples of gestational targets as outputs; and
determining the gestational target as a function of the gestational inquiry using a trained target machine-learning model; and
generating, using the at least a processor, a gestational report as a function of the gestational target.

12. The method of claim 11, wherein determining the gestational target comprises determining a nutritional threshold for the user.

13. The method of claim 11, wherein generating the gestational report comprises generating the gestational report using a large language model.

14. The method of claim 13, wherein determining the gestational target further comprises specifically training the target machine-learning model using training data, wherein the training data comprises a plurality of biological extractions from users within a same gestational phase as the user as inputs correlated to gestational targets as a outputs.

15. The method of claim 11, wherein determining the gestational target comprises identifying one or more gestational suggestions as a function of the gestational inquiry and the biological extraction.

16. The method of claim 15, wherein the gestational suggestion comprises a dietary suggestion.

17. The method of claim 15, wherein the gestational suggestion comprises a fitness suggestion.

18. The method of claim 11, wherein the biological extraction further comprises at least an element of physiological data.

19. The method of claim 11, the method further comprises determining, using the at least a processor, a gestational eligibility of the gestational target.

20. The method of claim 19, wherein determining the gestational eligibility of the gestational target further comprises evaluating at least a positive effect of the gestational target on the user's biological extraction and gestational phase.

* * * * *